(12) United States Patent
Halas et al.

(10) Patent No.: US 9,222,665 B2
(45) Date of Patent: Dec. 29, 2015

(54) WASTE REMEDIATION

(75) Inventors: Nancy J. Halas, Houston, TX (US); Peter Nordlander, Houston, TX (US); Oara Neumann, Houston, TX (US)

(73) Assignee: William Marsh Rice University, Houston, TX (US)

(*) Notice: Subject to any disclaimer, the term of this patent is extended or adjusted under 35 U.S.C. 154(b) by 106 days.

(21) Appl. No.: 13/326,482

(22) Filed: Dec. 15, 2011

(65) Prior Publication Data

US 2012/0156102 A1 Jun. 21, 2012

Related U.S. Application Data

(60) Provisional application No. 61/423,417, filed on Dec. 15, 2010.

(51) Int. Cl.
*A61L 2/07* (2006.01)
*F22B 1/28* (2006.01)
(Continued)

(52) U.S. Cl.
CPC . *F22B 1/281* (2013.01); *A61L 2/10* (2013.01); *A61L 11/00* (2013.01); *B09B 3/0075* (2013.01); *B09B 3/0091* (2013.01); *C02F 11/18* (2013.01); *F22B 1/006* (2013.01); *F24J 2/07* (2013.01); *F24J 2/42* (2013.01); *F24J 2/48* (2013.01); *B82Y 30/00* (2013.01); *C02F 2103/003* (2013.01); *C02F 2103/005* (2013.01); *C02F 2103/30* (2013.01); *C02F 2103/32* (2013.01); *C02F 2209/02* (2013.01); *C02F 2209/03* (2013.01); *C02F 2303/04* (2013.01); *F24J 2/14* (2013.01); *F24J 2/485* (2013.01);

(Continued)

(58) Field of Classification Search
CPC .............. A61L 2/07; A61L 2/10; F22B 1/281
USPC .......................................... 422/295, 26, 292
See application file for complete search history.

(56) References Cited

U.S. PATENT DOCUMENTS

| | | |
|---|---|---|
| 4,320,663 A | 3/1982 | Francia |
| 4,391,100 A | 7/1983 | Smith |

(Continued)

FOREIGN PATENT DOCUMENTS

| | | |
|---|---|---|
| EP | 2123968 A1 | 11/2009 |
| GB | 2456765 A | 7/2009 |

(Continued)

OTHER PUBLICATIONS

"Steam Sterilization" Sterile Processing University. 2007. retrieved from http://www.spdceus.com/pdf/steam_sterilization.pdf.*

(Continued)

*Primary Examiner* — Sean E Conley
*Assistant Examiner* — Donald Spamer
(74) *Attorney, Agent, or Firm* — Osha Liang LLP

(57) ABSTRACT

A system including a steam generation system and a chamber. The steam generation system includes a complex and the steam generation system is configured to receive water, concentrate electromagnetic (EM) radiation received from an EM radiation source, apply the EM radiation to the complex, where the complex absorbs the EM radiation to generate heat, and transform, using the heat generated by the complex, the water to steam. The chamber is configured to receive the steam and an object, wherein the object is of medical waste, medical equipment, fabric, and fecal matter.

13 Claims, 17 Drawing Sheets

(51) Int. Cl.
- *F24J 2/07* (2006.01)
- *F24J 2/42* (2006.01)
- *F24J 2/48* (2006.01)
- *A61L 2/10* (2006.01)
- *A61L 11/00* (2006.01)
- *C02F 11/18* (2006.01)
- *B09B 3/00* (2006.01)
- *F22B 1/00* (2006.01)
- *F24J 2/14* (2006.01)
- *F28F 13/18* (2006.01)
- *B82Y 30/00* (2011.01)
- *C02F 103/00* (2006.01)
- *C02F 103/30* (2006.01)
- *C02F 103/32* (2006.01)

(52) U.S. Cl.
CPC ............... *F28F 13/187* (2013.01); *Y02E 10/41* (2013.01); *Y02W 10/37* (2015.05)

(56) References Cited

U.S. PATENT DOCUMENTS

| | | | |
|---|---|---|---|
| 4,876,854 A | 10/1989 | Owens | |
| 5,241,824 A | 9/1993 | Parker et al. | |
| 5,419,135 A | 5/1995 | Wiggs | |
| 6,245,294 B1 * | 6/2001 | Goldberg et al. | 422/26 |
| 6,685,986 B2 | 2/2004 | Oldenburg et al. | |
| 7,247,953 B1 | 7/2007 | Schmulewitz | |
| 2003/0107741 A1 | 6/2003 | Pyo et al. | |
| 2005/0269316 A1 | 12/2005 | Monteleone et al. | |
| 2008/0138253 A1 * | 6/2008 | Golder et al. | 422/112 |
| 2008/0241262 A1 | 10/2008 | Lee et al. | |
| 2008/0308403 A1 | 12/2008 | Maloney et al. | |
| 2008/0318031 A1 | 12/2008 | Smith | |
| 2009/0179429 A1 | 7/2009 | Ellis et al. | |
| 2011/0180385 A1 | 7/2011 | Imholt | |
| 2011/0185728 A1 | 8/2011 | Meyers et al. | |
| 2011/0226440 A1 | 9/2011 | Bissell et al. | |
| 2011/0240104 A1 | 10/2011 | Lee et al. | |

FOREIGN PATENT DOCUMENTS

| | | |
|---|---|---|
| WO | 93/00781 A1 | 1/1993 |
| WO | 99/06322 A1 | 2/1999 |
| WO | 2008/104900 A2 | 9/2008 |
| WO | 2009/114567 A1 | 9/2009 |

OTHER PUBLICATIONS

Written Opinion of the International Searching Authority for International Application No. PCT/US2011/062507 mailed Mar. 6, 2012 (7 pages).

Written Opinion of the International Searching Authority for International Application No. PCT/US2011/062497 mailed Mar. 6, 2012 (7 pages).

Written Opinion of the International Searching Authority for International Application No. PCT/US2010/060477 mailed Mar. 2, 2012 (9 pages).

International Report on Patentability issued in PCT/US2011/062507 mailed Jun. 18, 2013 (9 pages).

International Search Report for PCT/US2011/062497 mailed Jun. 18, 2013 (9 pages).

Taylor, R., Phelan, P., Otanicar, T., Adrian, R., and Prasher, R; "Vapor Generation in a Nanoparticle Liquid Suspension Using a Focused, Continuous Laser," Applied Physics Letters, AIP, American Institute of Physics, vol. 95, No. 16, Oct. 21, 2009 (3 pages).

International Search Report for PCT/US2010/060477 mailed Mar. 2, 2012 (3 pages).

International Search Report for PCT/US20111062507 mailed Mar. 6, 2012 (3 pages).

International Search Report for PCT/US2011/062497 mailed Mar. 6, 2012 (3 pages).

Office Action issued in related U.S. Appl. No. 13/884,552, mailed Dec. 18, 2014 (16 pages).

* cited by examiner

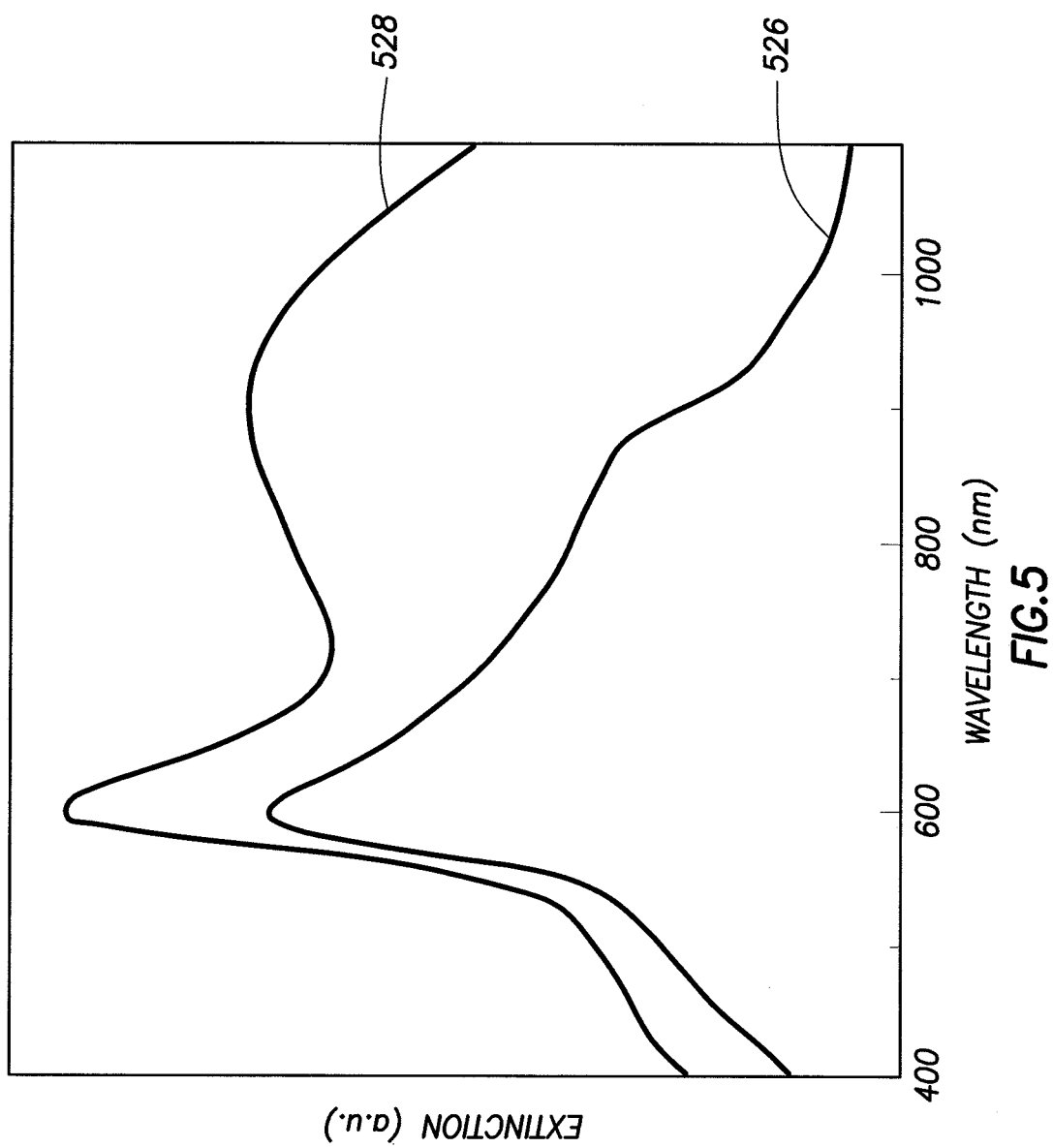

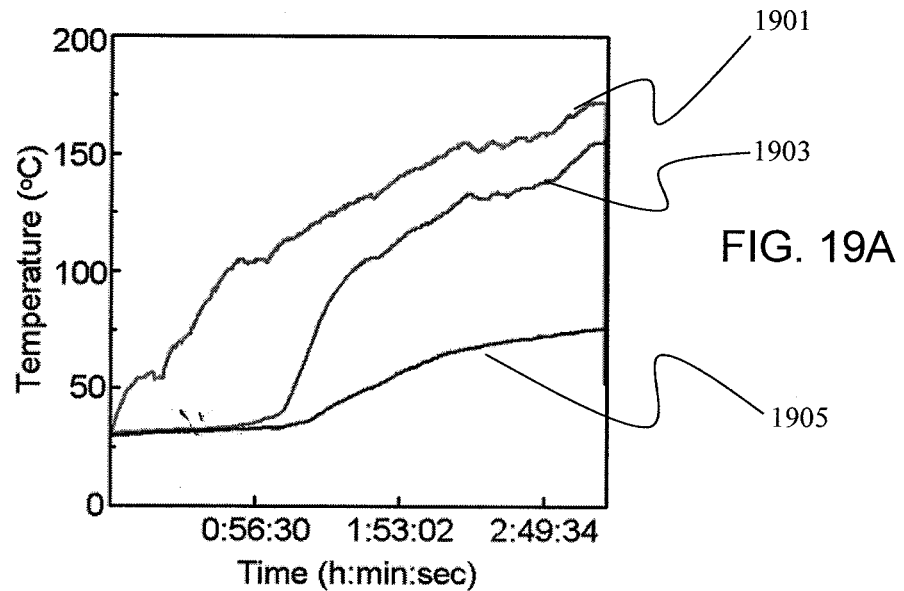
FIG. 19A
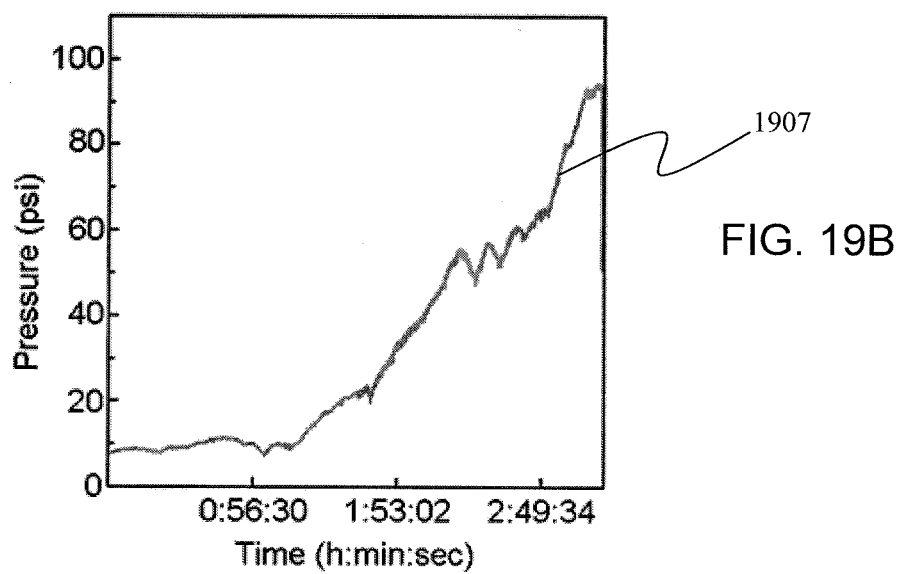
FIG. 19B
FIG. 19

WASTE REMEDIATION

CROSS REFERENCE TO RELATED APPLICATIONS

This application claims priority under 35 U.S.C. §119(e) to U.S. Provisional Patent Application Ser. No. 61/423,417, which is incorporated by reference in its entirety.

STATEMENT REGARDING FEDERALLY SPONSORED RESEARCH OR DEVELOPMENT

The invention was made with government support under Grant Number DE-AC52-06NA25396 awarded by the Department of Energy. The government has certain rights in the invention.

BACKGROUND

The disposal of waste and sterilization of equipment generally involves the generation of high temperature and/or pressure. For example, natural gas, coal, fuel oil, certain types of biomass, or some other suitable fuel may be combusted to supply high temperature/pressure vapor for the cleaning or disposal of waste. The combustion of the fuel may occur in a boiler, where the resulting heat is combined with fluid (commonly water) to generate vapor (commonly steam). Once the vapor reaches a certain temperature, the vapor may be used to clean equipment or decontaminate waste for disposal.

SUMMARY

In general, in one aspect, the invention relates to a system, comprising a steam generation system comprising a complex, wherein the steam generation system is configured to receive water, concentrate electromagnetic (EM) radiation received from an EM radiation source, apply the EM radiation to the complex, wherein the complex absorbs the EM radiation to generate heat, and transform, using the heat generated by the complex, the water to steam, and a chamber configured to receive the steam and an object, wherein the object is one selected from a group consisting of medical waste, medical equipment, fabric, and fecal matter, wherein the complex is at least one selected from a group consisting of copper nanoparticles, copper oxide nanoparticles, nanoshells, nanorods, carbon moieties, encapsulated nanoshells, encapsulated nanoparticles, and branched nanostructures.

In general, in one aspect, the invention relates to a system, comprising a water heater comprising a complex, wherein the system is configured to receive cold water, concentrate electromagnetic (EM) radiation received from an EM radiation source, apply the EM radiation to the complex, wherein the complex absorbs the EM radiation to generate heat and wherein the complex is at least one selected from a group consisting of copper nanoparticles, copper oxide nanoparticles, nanoshells, nanorods, carbon moieties, encapsulated nanoshells, encapsulated nanoparticles, and branched nanostructures, and heat the cold water using the heat generated by the complex, to generate warm water, and a steam generating system configured to receive the warm water from the water heater and generate steam using the warm water, a chamber configured to receive the steam and an object, wherein the object is one selected from a group consisting of medical waste, medical equipment, fabric, and fecal matter.

In general, in one aspect, the invention relates to a system, comprising a chamber comprising a complex wherein the chamber is configured to receive water and an object, wherein the object is one selected from a group consisting of medical waste, medical equipment, fabric, and fecal matter, a concentrator configured to concentrate electromagnetic (EM) radiation received from an EM radiation source and provide the concentrated EM radiation to the complex, wherein the complex absorbs the EM radiation to generate heat, and wherein the heat transforms the water to steam in the chamber, and wherein the object is exposed to the steam, wherein the complex is at least one selected from a group consisting of copper nanoparticles, copper oxide nanoparticles, nanoshells, nanorods, carbon moieties, encapsulated nanoshells, encapsulated nanoparticles, and branched nanostructures.

Other aspects of the invention will be apparent from the following description and the appended claims.

BRIEF DESCRIPTION OF DRAWINGS

FIG. 5 shows a chart of the absorbance in accordance with one or more embodiments of the invention.

FIGS. 19A and 19B show the temperature and pressure as a function of time in accordance with one or more embodiments of the invention.

DETAILED DESCRIPTION

Figure 1:
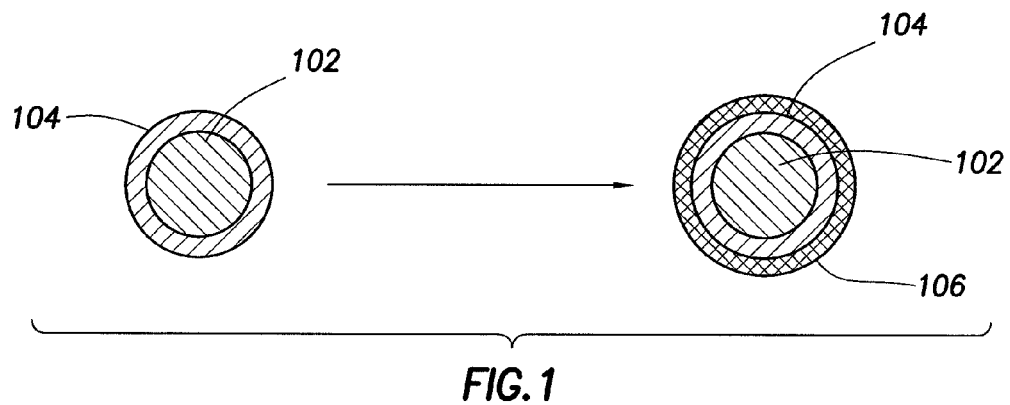
FIG. 1 shows a schematic of a complex in accordance with one or more embodiments of the invention.

Specific embodiments of the invention will now be described in detail with reference to the accompanying figures. Like elements in the various figures are denoted by like reference numerals for consistency.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

In general, embodiments of the invention provide for a system for waste disposal or remediation and/or object sterilization or sanitization using an electromagnetic (EM) radiation-absorbing complex. More specifically, one or more embodiments of the invention provide for creating a vapor (e.g., steam) from a fluid (e.g., water) by heating the fluid using one or more complexes (e.g., nanoshells) that have absorbed EM radiation.

The invention may provide for a complex mixed in a liquid solution, used to coat a wall of a vessel, integrated with a material of which a vessel is made, and/or otherwise suitably integrated with a vessel used to apply EM radiation to the complex. All the piping and associated fittings, pumps, valves, gauges, and other equipment described, used, or contemplated herein, either actually or as one of ordinary skill in the art would conceive, are made of materials resistant to the heat and/or chemicals transported, transformed, pressurized, created, or otherwise handled within those materials.

A source of EM radiation may be any source capable of emitting energy at one or more wavelengths. For example, EM radiation may be any source that emits radiation in the ultraviolet, visible, and infrared regions of the electromagnetic spectrum. A source of EM radiation may be manmade or occur naturally. Examples of a source of EM radiation may include, but are not limited to, the sun, waste heat from an industrial process, and a light bulb. One or more concentrators may be used to intensify and/or concentrate the energy emitted by a source of EM radiation. Examples of a concentrator include, but are not limited to, lens(es), a parabolic trough(s), mirror(s), black paint, or any combination thereof.

Embodiments of this invention may be used in any commercial and/or industrial application where waste disposal, remediation, sanitization, or sterilization may be required. Examples of such applications include, but are not limited to, sterilizing or sanitizing medical equipment, fabric, plastics, and/or fecal sludge/matter. Embodiments of this invention may also be used for processing and manufacturing for a number of market sectors (e.g., food processing and packaging, pulp and paper, printing, chemicals and allied products, rubber, plastics, cosmetics, textile production, electronics), hospitals, universities, drug manufacturing, wastewater and sewage treatment, and beverages.

In one or more embodiments, the complex may include one or more nanoparticle structures including, but not limited to, nanoshells, coated nanoshells, metal colloids, nanorods, branched or coral structures, and/or carbon moieties. In one or more embodiments, the complex may include a mixture of nanoparticle structures to absorb EM radiation. Specifically, the complex may be designed to maximize the absorption of the electromagnetic radiation emitted from the sun. Further, each complex may absorb EM radiation over a specific range of wavelengths.

In one or more embodiments, the complex may include metal nanoshells. A nanoshell is a substantially spherical dielectric core surrounded by a thin metallic shell. The plasmon resonance of a nanoshell may be determined by the size of the core relative to the thickness of the metallic shell. Nanoshells may be fabricated according to U.S. Pat. No. 6,685,986, hereby incorporated by reference in its entirety. The relative size of the dielectric core and metallic shell, as well as the optical properties of the core, shell, and medium, determines the plasmon resonance of a nanoshell. Accordingly, the overall size of the nanoshell is dependent on the absorption wavelength desired. Metal nanoshells may be designed to absorb or scatter light throughout the visible and infrared regions of the electromagnetic spectrum. For example, a plasmon resonance in the near infrared region of the spectrum (700 nm-900 nm) may have a substantially spherical silica core having a diameter between 90 nm-175 nm and a gold metallic layer between 4 nm-35 nm.

A complex may also include other core-shell structures, for example, a metallic core with one or more dielectric and/or metallic layers using the same or different metals. For example, a complex may include a gold or silver nanoparticle, spherical or rod-like, coated with a dielectric layer and further coated with another gold or silver layer. A complex may also include other core-shell structures, for example hollow metallic shell nanoparticles and/or multi-layer shells.

In one or more embodiments, a complex may include a nanoshell encapsulated with a dielectric or rare earth element oxide. For example, gold nanoshells may be coated with an additional shell layer made from silica, titanium or europium oxide.

In one embodiment of the invention, the complexes may be aggregated or otherwise combined to create aggregates. In such cases, the resulting aggregates may include complexes of the same type or complexes of different types.

In one embodiment of the invention, complexes of different types may be combined as aggregates, in solution, or embedded on substrate. By combining various types of complexes, a broad range of the EM spectrum may be absorbed FIG. 1 is a schematic of a nanoshell coated with an additional rare earth element oxide in accordance with one or more embodiments of the invention. Typically, a gold nanoshell has a silica core 102 surrounded by a thin gold layer 104. As stated previously, the size of the gold layer is relative to the size of the core and determines the plasmon resonance of the particle. According to one or more embodiments of the invention, a nanoshell may then be coated with a dielectric or rare earth layer 106. The additional layer 106 may serve to preserve the resultant plasmon resonance and protect the particle from any temperature effects, for example, melting of the gold layer 104.

Figure 2:
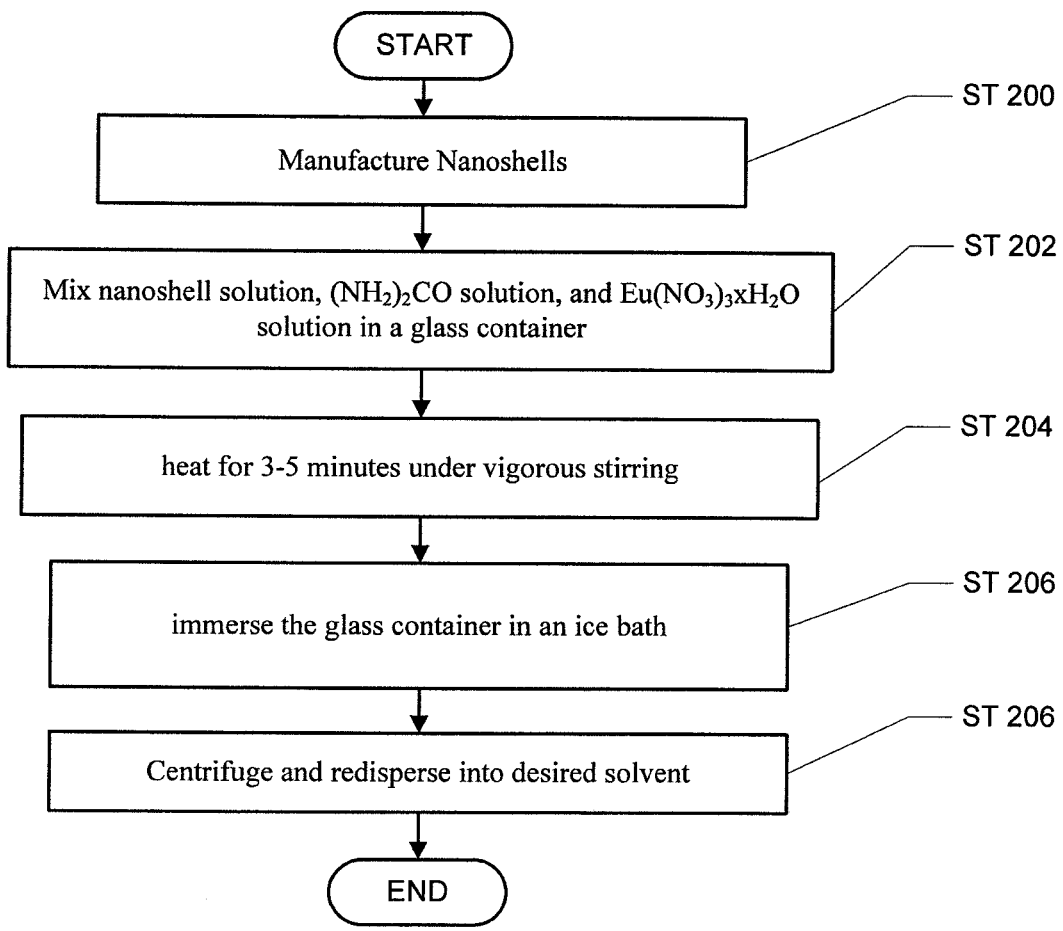
FIG. 2 shows a flow chart in accordance with one or more embodiments of the invention.

FIG. 2 is a flow chart of a method of manufacturing the coated nanoshells in accordance with one or more embodiments of the invention. In ST 200, nanoshells are manufactured according to known techniques. In the example of europium oxide, in ST 202, 20 mL of a nanoshell solution may be mixed with 10 mL of 2.5M $(NH_2)_2CO$ and 20 mL of 0.1M of $Eu(NO_3)_3 \times H_2O$ solutions in a glass container. In ST 204, the mixture may be heated to boiling for 3-5 minutes under vigorous stirring. The time the mixture is heated may determine the thickness of the additional layer, and may also determine the number of nanoparticle aggregates in solution. The formation of nanostructure aggregates is known to create additional plasmon resonances at wavelengths higher than the individual nanostructure that may contribute to the energy absorbed by the nanostructure for heat generation. In ST 206, the reaction may then be stopped by immersing the glass container in an ice bath. In ST 208, the solution may then be cleaned by centrifugation, and then redispersed into the desired solvent. The additional layer may contribute to the solubility of the nanoparticles in different solvents. Solvents that may be used in one or more embodiments of the invention include, but are not limited to, water, ammonia, ethylene glycol, and glycerin.

In addition to europium, other examples of element oxides that may be used in the above recipe include, but are not limited to, erbium, samarium, praseodymium, and dysprosium. The additional layer is not limited to rare earth oxides. Any coating of the particle that may result in a higher melting point, better solubility in a particular solvent, better deposition onto a particular substrate, and/or control over the number of aggregates or plasmon resonance of the particle may be used. Examples of the other coatings that may be used, but are not limited to silica, titanium dioxide, polymer-based coatings, additional layers formed by metals or metal alloys, and/or combinations of materials.

Figure 3:
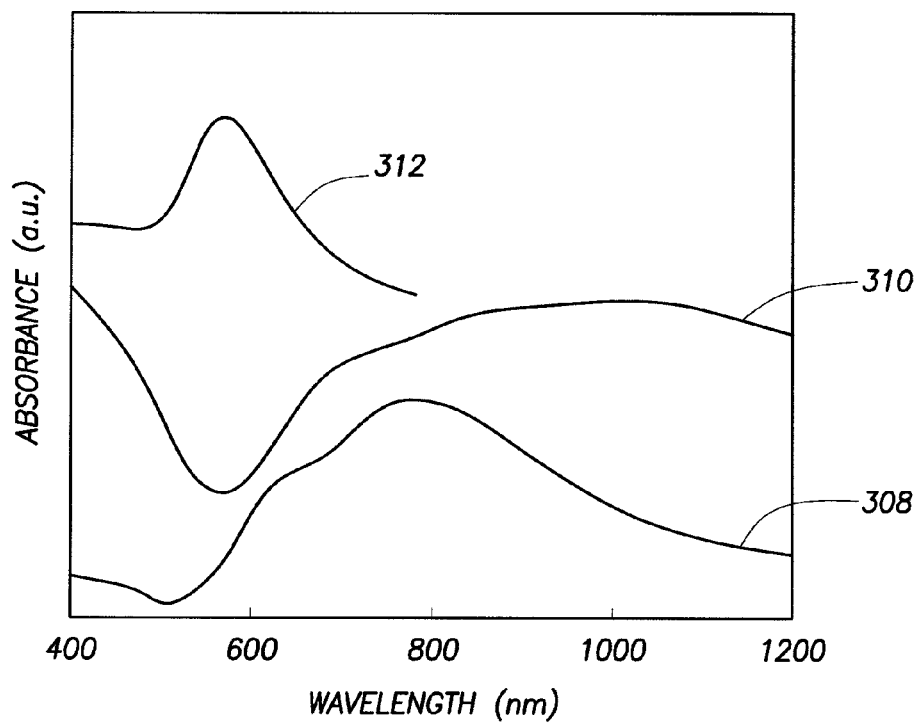
FIG. 3 shows a chart of the absorbance in accordance with one or more embodiments of the invention.

FIG. 3 is an absorbance spectrum of three nanoparticle structures that may be included in a complex in accordance with one or more embodiments disclosed herein. In FIG. 3, a gold nanoshell spectrum 308 may be engineered by selecting the core and shell dimensions to obtain a plasmon resonance peak at ~800 nm. FIG. 3 also includes a $Eu_2O_3$-encapsulated gold nanoshell spectrum 310, where the $Eu_2O_3$-encapsulated gold nanoshell is manufactured using the same nanoshells from the nanoshell spectrum 308. As may be seen in FIG. 3, there may be some particle aggregation in the addition of the europium oxide layer. However, the degree of particle aggregation may be controlled by varying the reaction time described above. FIG. 3 also includes a ~100 nm diameter spherical gold colloid spectrum 312 that may be used to absorb electromagnetic radiation in a different region of the electromagnetic spectrum. In the specific examples of FIG. 3, the $Eu_2O_3$-encapsulated gold nanoshells may be mixed with the gold colloids to construct a complex that absorbs any EM radiation from 500 nm to greater than 1200 nm. The concentrations of the different nanoparticle structures may be manipulated to achieve the desired absorption of the complex.

Figure 4A:
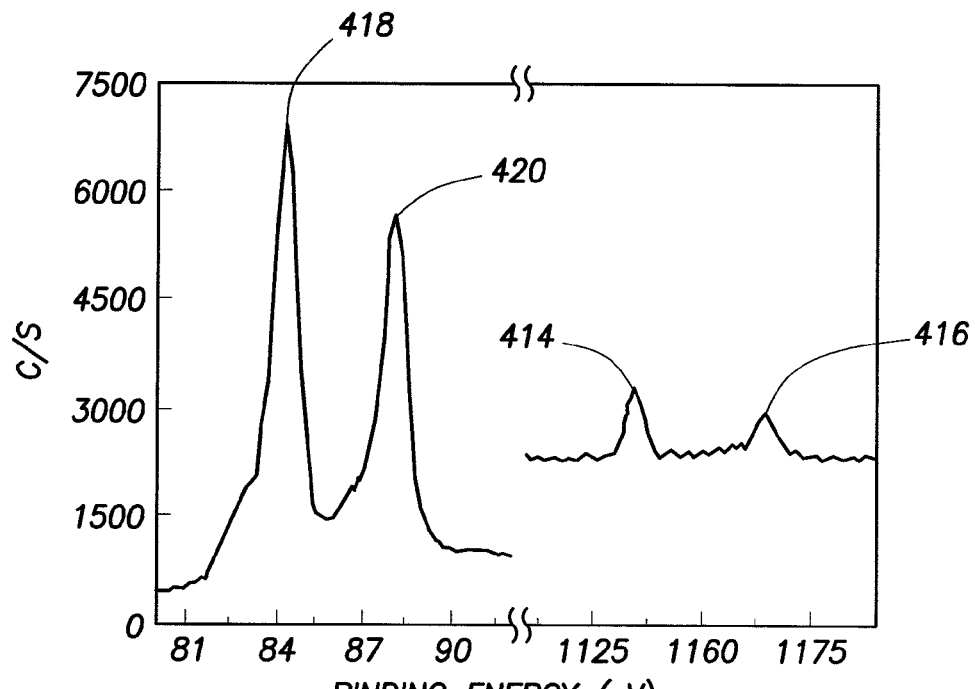
FIGS. 4A-4B show charts of an energy dispersive x-ray spectroscopy (EDS) measurement in accordance with one or more embodiments of the invention.
Figure 4B:
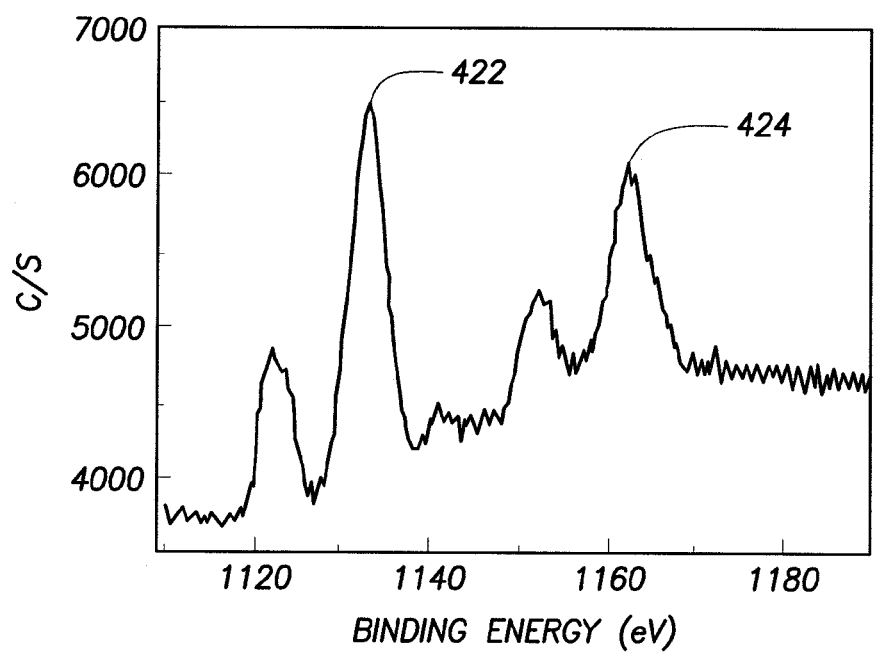

X-ray photoelectron spectroscopy (XPS) and/or energy dispersive x-ray spectroscopy (EDS) measurements may be used to investigate the chemical composition and purity of the nanoparticle structures in the complex. For example, FIG. 4A shows an XPS spectrum in accordance with one or more embodiments of the invention. XPS measurements were acquired with a PHI Quantera X-ray photoelectron spectrometer. FIG. 4A shows the XPS spectra in different spectral regions corresponding to the elements of the nanoshell encapsulated with europium oxide. FIG. 4A shows the XPS spectra display the binding energies for Eu (3d 5/2) at 1130 eV 414, Eu (2d 3/2) at 1160 eV 416, Au (4f 7/2) at 83.6 eV 418, and Au (4f 5/2) at 87.3 eV 420 of nanoshells encapsulated with europium oxide. For comparison, FIG. 4B shows an XPS spectrum of europium oxide colloids that may be manufactured according to methods known in the art. FIG. 4B shows the XPS spectra display the binding energies for Eu (3d 5/2) at 1130 eV 422 and Eu (2d 3/2) at 1160 eV 424 of europium oxide colloids.

In one or more embodiments of the invention, the complex may include solid metallic nanoparticles encapsulated with an additional layer as described above. For example, using the methods described above, solid metallic nanoparticles may be encapsulated using silica, titanium, europium, erbium, samarium, praseodymium, and dysprosium. Examples of solid metallic nanoparticles include, but are not limited to, spherical gold, silver, copper, or nickel nanoparticles or solid metallic nanorods. The specific metal may be chosen based on the plasmon resonance, or absorption, of the nanoparticle when encapsulated. The encapsulating elements may be chosen based on chemical compatibility, the encapsulating elements ability to increase the melting point of the encapsulated nanoparticle structure, and the collective plasmon resonance, or absorption, of a solution of the encapsulated nanostructure, or the plasmon resonance of the collection of encapsulated nanostructures when deposited on a substrate.

In one or more embodiments, the complex may also include copper colloids. Copper colloids may be synthesized using a solution-phase chemical reduction method. For example, 50 mL of 0.4 M aqueous solution of L-ascorbic acid, 0.8M of Polyvinyl pyridine (PVP), and 0.01M of copper (II) nitride may be mixed and heated to 70 degree Celsius until the solution color changes from a blue-green color to a red color. The color change indicates the formation of copper nanoparticles. FIG. 5 is an experimental and theoretical spectrum in accordance with one or more embodiments of the invention. FIG. 5 includes an experimental absorption spectrum 526 of copper colloids in accordance with one or more embodiments of the invention. Therefore, copper colloids may be used to absorb electromagnetic radiation in the 550 nm to 900 nm range.

FIG. 5 also includes a theoretical absorption spectrum 528 calculated using Mie scattering theory. In one or more embodiments, Mie scattering theory may be used to theoretically determine the absorbance of one or more nanoparticle structures to calculate and predict the overall absorbance of the complex. Thus, the complex may be designed to maximize the absorbance of solar electromagnetic radiation.

Figure 6:
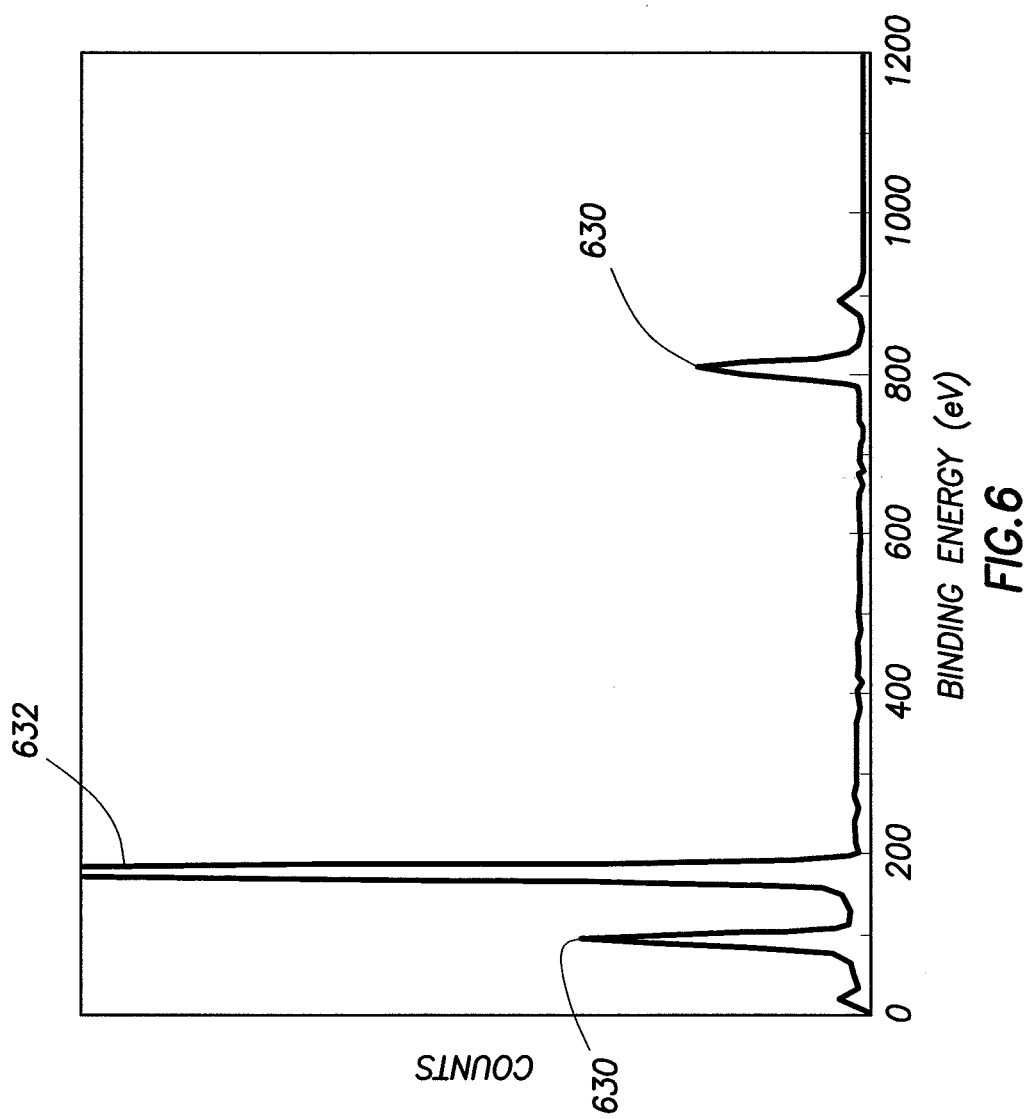
FIG. 6 shows a chart of an EDS measurement in accordance with one or more embodiments of the invention.

Referring to FIG. 6, an EDS spectrum of copper colloids in accordance with one or more embodiments of the invention is shown. The EDS spectrum of the copper colloids confirms the existence of copper atoms by the appearance peaks 630. During the EDS measurements, the particles are deposited on a silicon substrate, as evidenced by the presence of the silicon peak 632.

Figure 7:
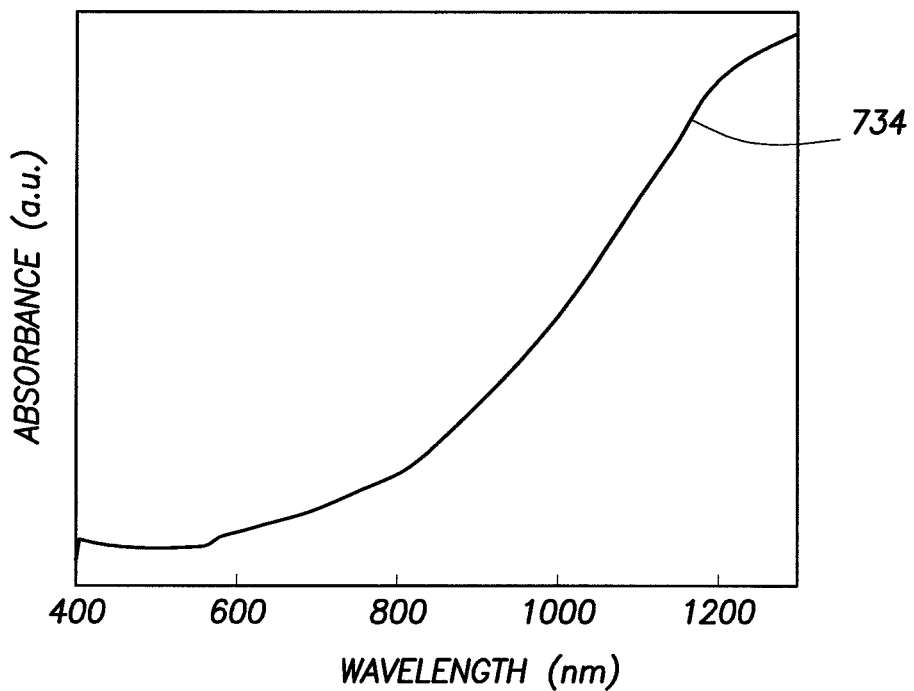
FIG. 7 shows a chart of the absorbance in accordance with one or more embodiments of the invention.

In one or more embodiments, the complex may include copper oxide nanoparticles. Copper oxide nanostructures may be synthesized by 20 mL aqueous solution of 62.5 mM $Cu(NO_3)_2$ being directly mixed with 12 mL $NH_4OH$ under stirring. The mixture may be stirred vigorously at approximately 80° C. for 3 hours, then the temperature is reduced to 40° C. and the solution is stirred overnight. The solution color turns from blue to black color indicating the formation of the copper oxide nanostructure. The copper oxide nanostructures may then be washed and resuspended in water via centrifugation. FIG. 7 shows the absorption of copper oxide nanoparticles in accordance with one or more embodiments of the invention. The absorption of the copper oxide nanoparticles 734 may be used to absorb electromagnetic radiation in the region from ~900 nm to beyond 1200 nm.

Figure 8:
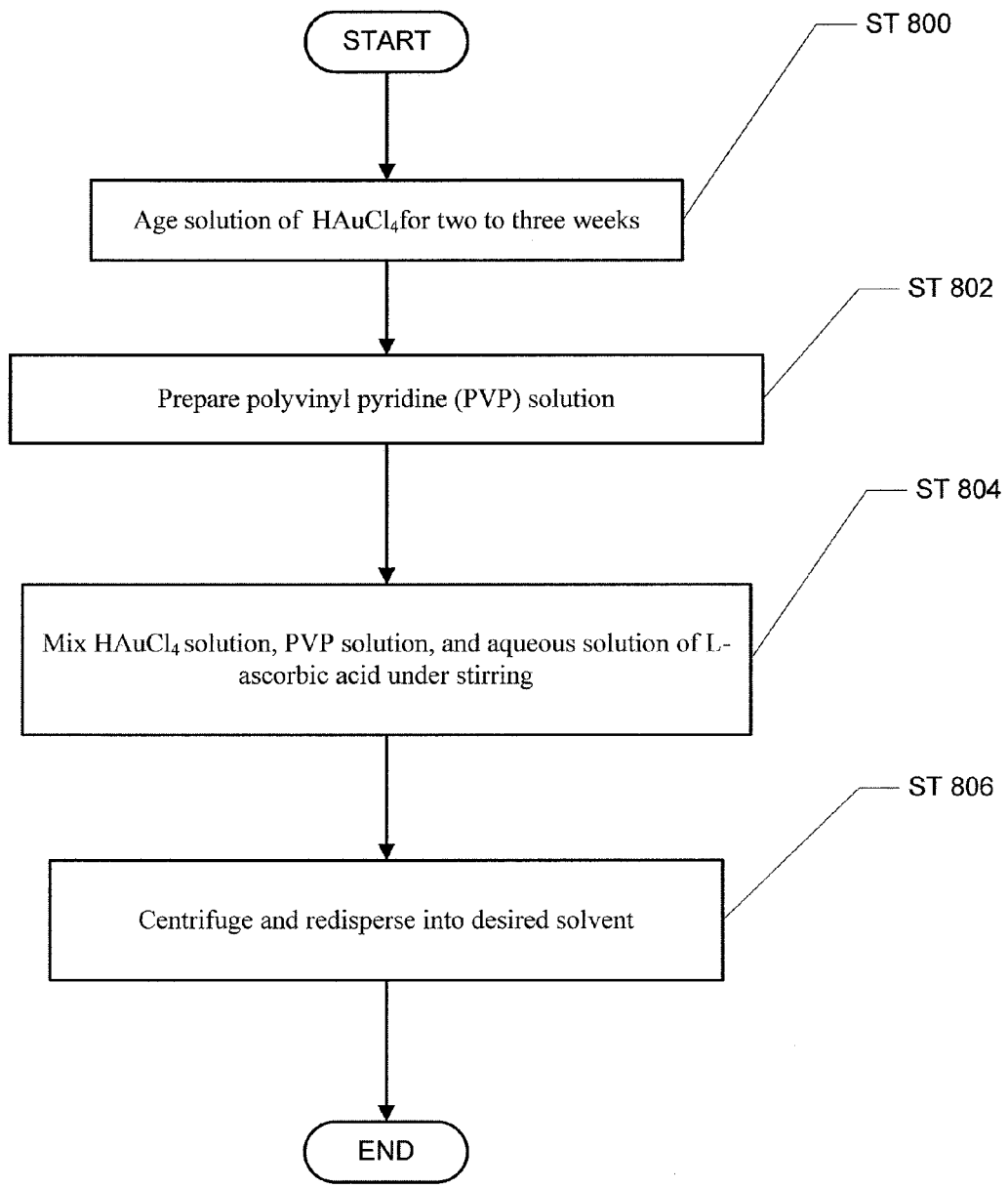
FIG. 8 shows a flow chart in accordance with one or more embodiments of the invention.

In one or more embodiments of the invention, the complex may include branched nanostructures. One of ordinary skill in the art will appreciate that embodiments of the invention are not limited to strict gold branched structures. For example, silver, nickel, copper, or platinum branched structures may also be used. FIG. 8 is a flow chart of the method of manufacturing gold branched structures in accordance with one or more embodiments of the invention. In ST 800, an aqueous solution of 1% $HAuCl_4$ may be aged for two-three weeks. In ST 802, a polyvinyl pyridine (PVP) solution may be prepared by dissolving 0.25 g in approximately 20 mL ethanol solution and rescaled with water to a final volume of 50 mL In ST 804, 50 mL of the 1% $HAuCl_4$ and 50 mL of the PVP solution may be directly mixed with 50 mL aqueous solution of 0.4M L-ascorbic acid under stirring. The solution color may turn immediately in dark blue-black color which indicates the formation of a gold nanoflower or nano-coral. Then, in ST 806, the Au nanostructures may then be washed and resuspended in water via centrifugation. In other words, the gold branched nanostructures may be synthesized through L-ascorbic acid reduction of aqueous chloroaurate ions at room temperature with addition of PVP as the capping agent. The capping polymer PVP may stabilize the gold branched nanostructures by preventing them from aggregating. In addition, the gold branched nanostructures may form a porous polymer-type matrix.

Figure 9:
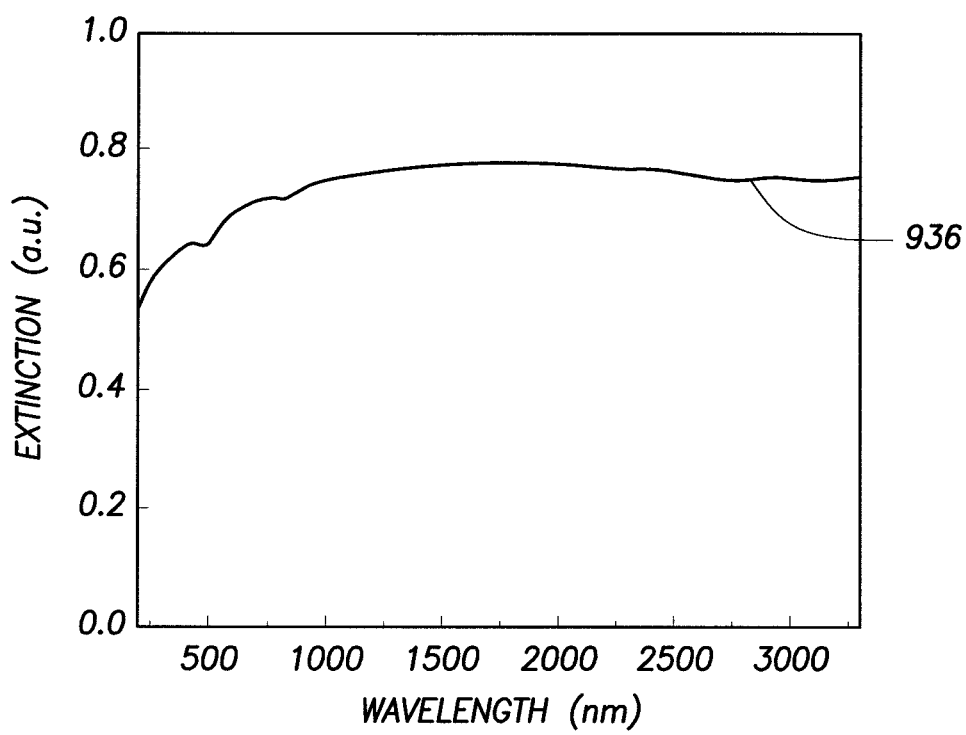
FIG. 9 shows a chart of the absorbance in accordance with one or more embodiments of the invention.

FIG. 9 shows the absorption of a solution of gold branched nanostructures in accordance with one or more embodiments of the invention. As can be seen in FIG. 9, the absorption spectrum 936 of the gold branched nanostructures is almost flat for a large spectral range, which may lead to considerably high photon absorption. The breadth of the spectrum 936 of the gold branched nanostructures may be due to the structural diversity of the gold branched nanostructures or, in other works, the collective effects of which may come as an average of individual branches of the gold branched/corals nanostructure.

Figure 10:
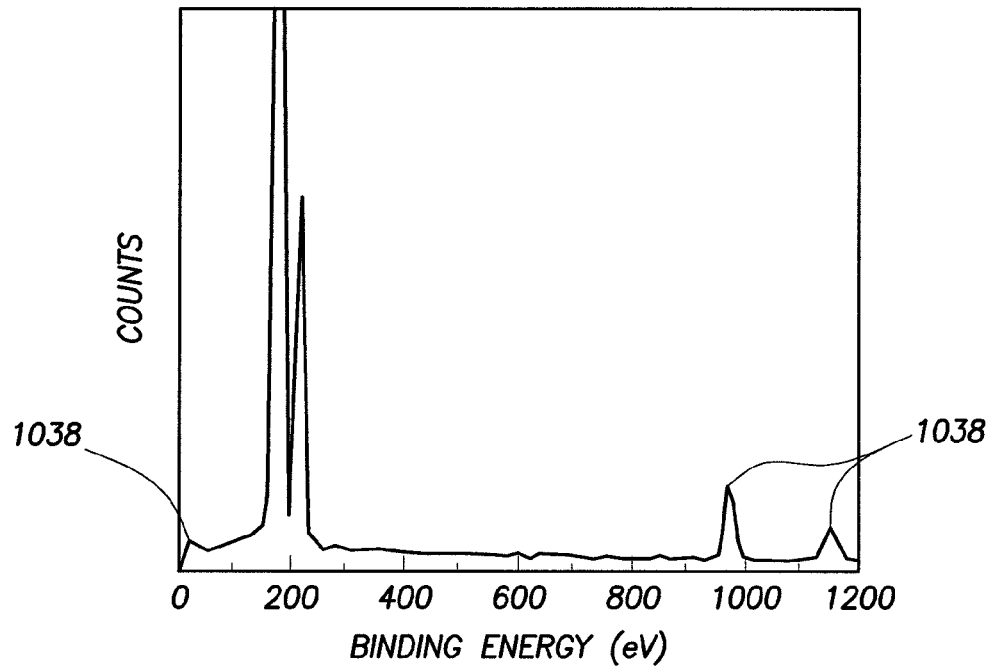
FIG. 10 shows a chart of an EDS measurement in accordance with one or more embodiments of the invention.

FIG. 10 shows the EDS measurements of the gold branched nanostructures in accordance with one or more embodiments of the invention. The EDS measurements may be performed to investigate the chemical composition and purity of the gold branched nanostructures. In addition, the peaks 1038 in the EDS measurements of gold branched nanostructures confirm the presence of Au atoms in the gold branched nanostructures.

Figure 11A:
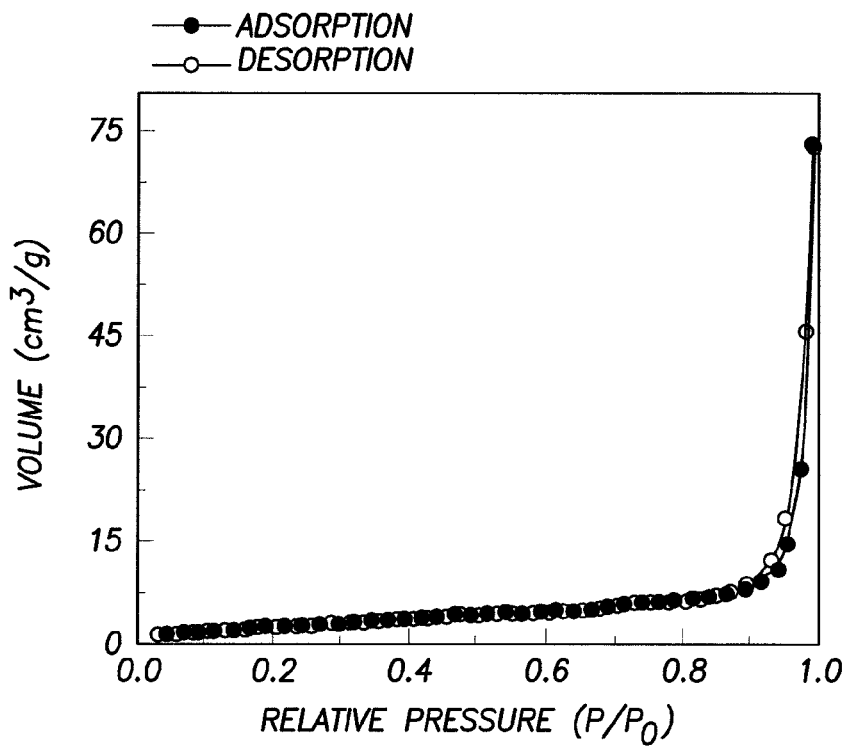
FIGS. 11A-11C show charts of the porosity of gold corral structures in accordance with one or more embodiments of the invention.
Figure 11B:
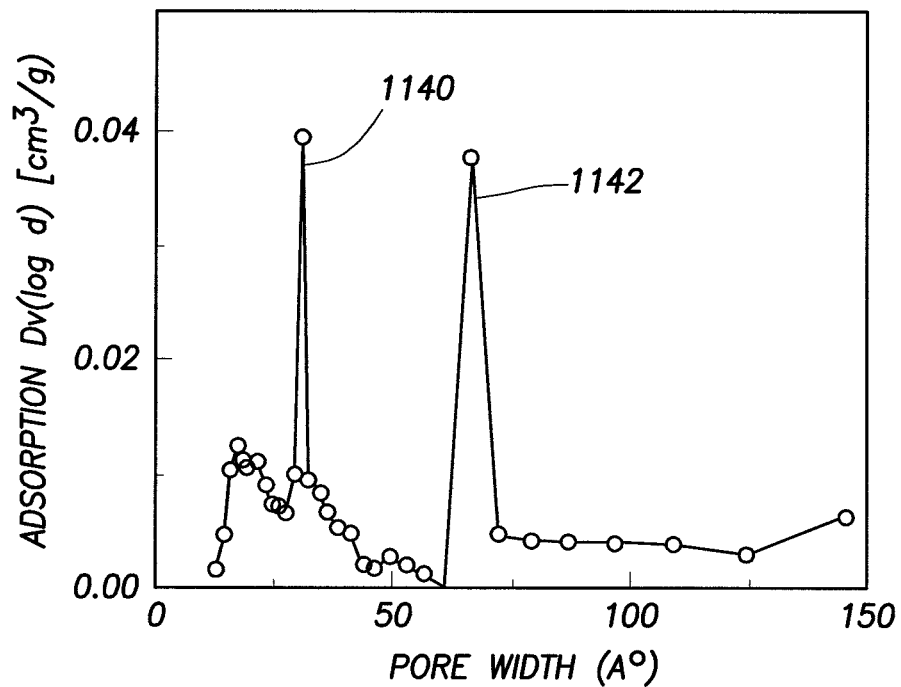
Figure 11C:
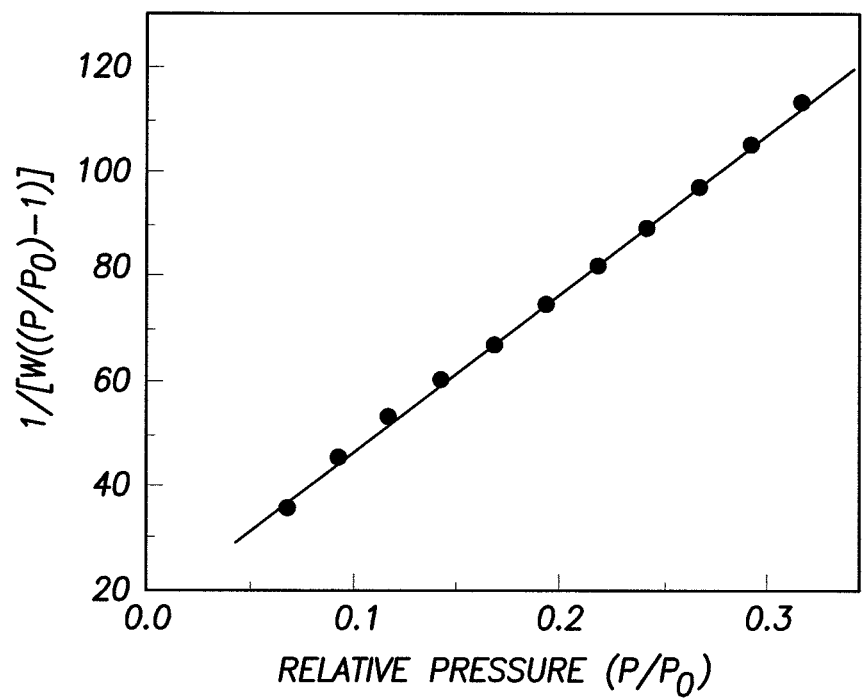

FIG. 11 shows a Brunauer-Emmett-Teller (BET) surface area and pore size distribution analysis of branches in accordance with one or more embodiments of the invention. The BET surface area and pore size may be performed to characterize the branched nanostructures. FIG. 11A presents the nitrogen adsorption-desorption isotherms of a gold corral sample calcinated at 150° C. for 8 hours. The isotherms may exhibit a type IV isotherm with a $N_2$ hysteresis loops in desorption branch as shown. As shown in FIG. 11A, the isotherms may be relatively flat in the low-pressure region ($P/P_0$<0.7). Also, the adsorption and desorption isotherms may be completely superposed, a fact which may demonstrate that the adsorption of the samples mostly likely occurs in the pores. At the relative high pressure region, the isotherms may form a loop due to the capillarity agglomeration phenomena. FIG. 11B presents a bimodal pore size distribution, showing the first peak 1140 at the pore diameter of 2.9 nm and the second peak 1142 at 6.5 nm. FIG. 11C shows the BET plots of gold branched nanostructures in accordance with one or more embodiments of the invention. A value of 10.84 $m^2$/g was calculated for the specific surface area of branches in this example by using a multipoint BET-equation.

In one or more embodiments of the invention, the gold branched nanostructures dispersed in water may increase the nucleation sites for boiling, absorb electromagnetic energy, decrease the bubble lifetime due to high surface temperature and high porosity, and increase the interfacial turbulence by the water gradient temperature and the Brownian motion of the particles. The efficiency of a gold branched complex solution may be high because it may allow the entire fluid to be involved in the boiling process.

As demonstrated in the above figures and text, in accordance with one or more embodiments of the invention, the complex may include a number of different specific nanostructures chosen to maximize the absorption of the complex in a desired region of the electromagnetic spectrum. In addition, the complex may be suspended in different solvents, for example water or ethylene glycol. Also, the complex may be deposited onto a surface according to known techniques. For example, a molecular or polymer linker may be used to fix the complex to a surface, while allowing a solvent to be heated when exposed to the complex. The complex may also be embedded in a matrix or porous material. For example, the complex may be embedded in a polymer or porous matrix material formed to be inserted into a particular embodiment as described below. For example, the complex could be formed into a removable cartridge. As another example, a porous medium (e.g., fiberglass) may be embedded with the complex and placed in the interior of a vessel containing a fluid to be heated. The complex may also be formed into shapes in one or more embodiments described below in order to maximize the surface of the complex and, thus, maximize the absorption of EM radiation. In addition, the complex may be embedded in a packed column or coated onto rods inserted into one or more embodiments described below.

Figure 12A:
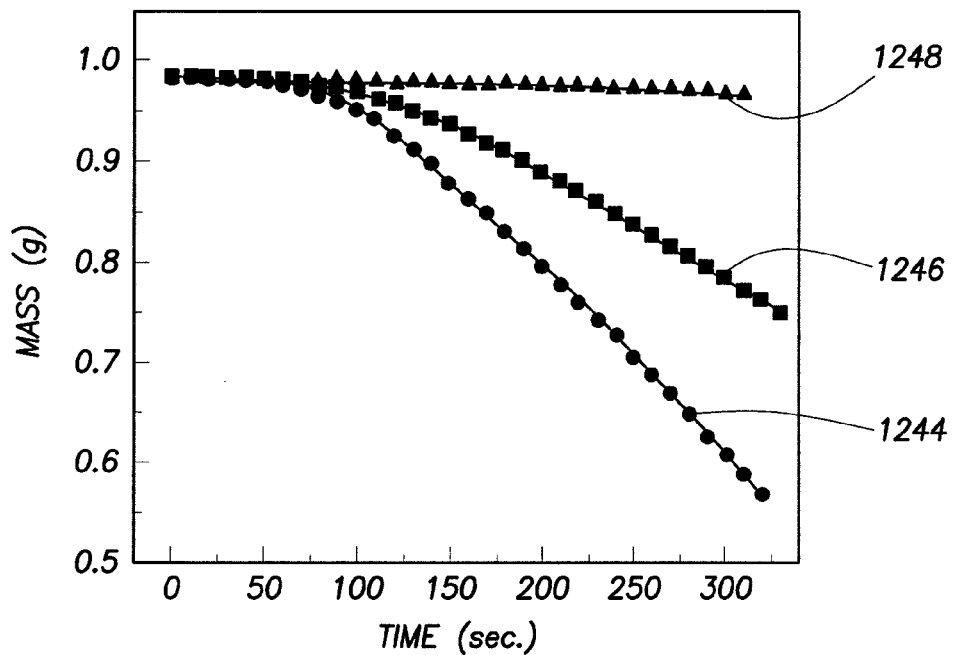
FIGS. 12A-12C show charts of the mass loss of water into steam in accordance with one or more embodiments of the invention.
Figure 12B:
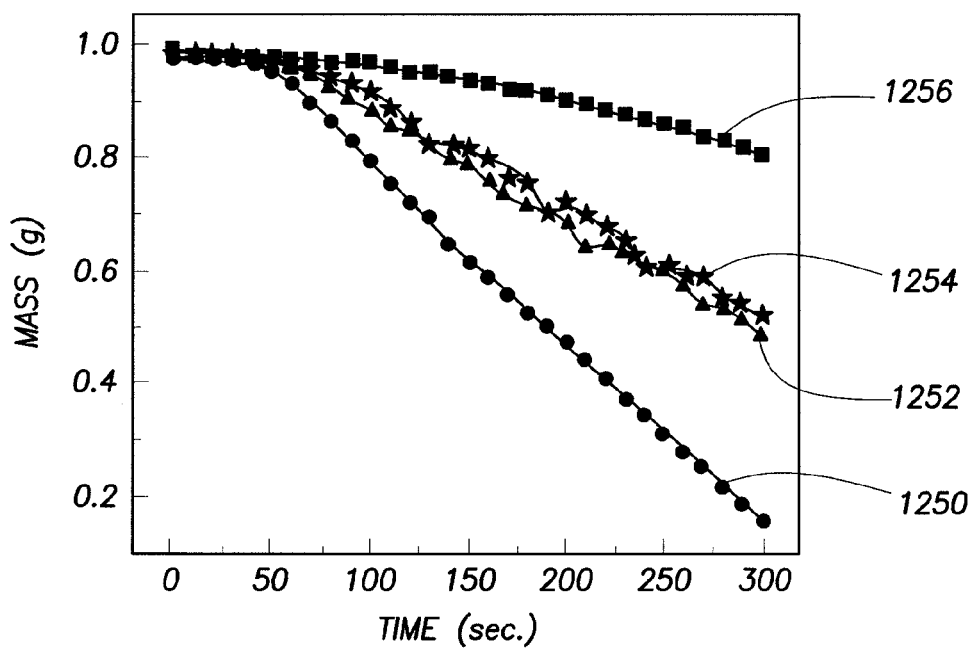
Figure 12C:
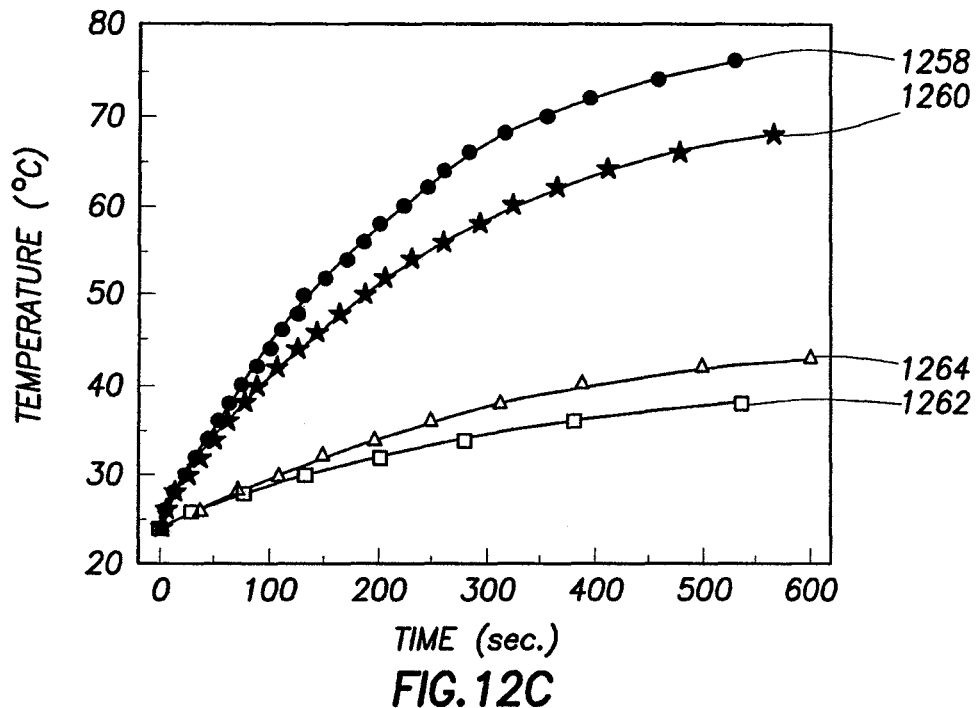

FIGS. 12A-12C show charts of the mass loss and temperature increase of different nanostructures that may be used in a complex in accordance with one or more embodiments of the invention. The results shown in FIGS. 12A-12C were performed to monitor the mass loss of an aqueous nanostructure solution for 10 minutes under sunlight (FIG. 12B) versus non-pulsed diode laser illumination at 808 nm (FIG. 12A). In FIG. 12A, the mass loss versus time of the laser illumination at 808 nm is shown for $Eu_2O_3$-coated nanoshells 1244, non-coated gold nanoshells 1246, and gold nanoparticles with a diameter of ~100 nm 1248. Under laser exposure, as may be expected from the absorbance shown in FIG. 3, at 808 nm illumination, the coated and non-coated nanoshells exhibit a mass loss due to the absorbance of the incident electromagnetic radiation at 808 nm. In addition, as the absorbance is lower at 808 nm, the 100 nm diameter gold colloid exhibits little mass loss at 808 nm illumination. In FIG. 12A, the Au nanoparticles demonstrated a lower loss rate that was nearly the same as water because the laser wavelength was detuned from plasmon resonance frequency. The greatest mass loss was obtained by adding a layer around the gold nanoshells, where the particle absorption spectrum was approximately the same as the solar spectrum (see FIG. 3.)

In FIG. 12B, the mass loss as a function of time under exposure to the sun in accordance with one or more embodiments of the invention is shown. In FIG. 12B, the mass loss under sun exposure with an average power of 20 W is shown for $Eu_2O_3$-coated nanoshells 1250, non-coated gold nanoshells 1252, gold nanoparticles with a diameter of ~100 nm 1254, and a water control 1256. As in the previous example, the greatest mass loss may be obtained by adding a rare earth or dielectric layer around a nanoshell.

The resulting mass loss curves in FIGS. 12A and 12B show significant water evaporation rates for $Eu_2O_3$-coated gold nanoshells. The mass loss may be slightly greater under solar radiation because the particles were able to absorb light from a broader range of wavelengths. In addition, the collective effect of aggregates broadens the absorption spectrum of the oxide-coated nanoparticles, which may help to further amplify the heating effect and create local areas of high temperature, or local hot spots. Aggregates may also allow a significant increase in boiling rates due to collective self organizing forces. The oxide layer may further enhance steam generation by increasing the surface area of the nanoparticle, thus providing more boiling nucleation sites per particle, while conserving the light-absorbing properties of nanostructure.

FIG. 12C shows the temperature increase versus time under the 808 nm laser exposure in accordance with one or more embodiments of the invention. In FIG. 12C, the temperature increase under the 808 nm laser exposure is shown for $Eu_2O_3$-coated nanoshells 1258, non-coated gold nanoshells 1260, gold nanoparticles with a diameter of ~100 nm 1262, and a water control 1264. As may be expected, the temperature of the solutions of the different nanostructures that may be included in the complex increases due to the absorption of the incident electromagnetic radiation of the specific nanostructure and the conversion of the absorbed electromagnetic radiation in to heat.

Figure 13B:
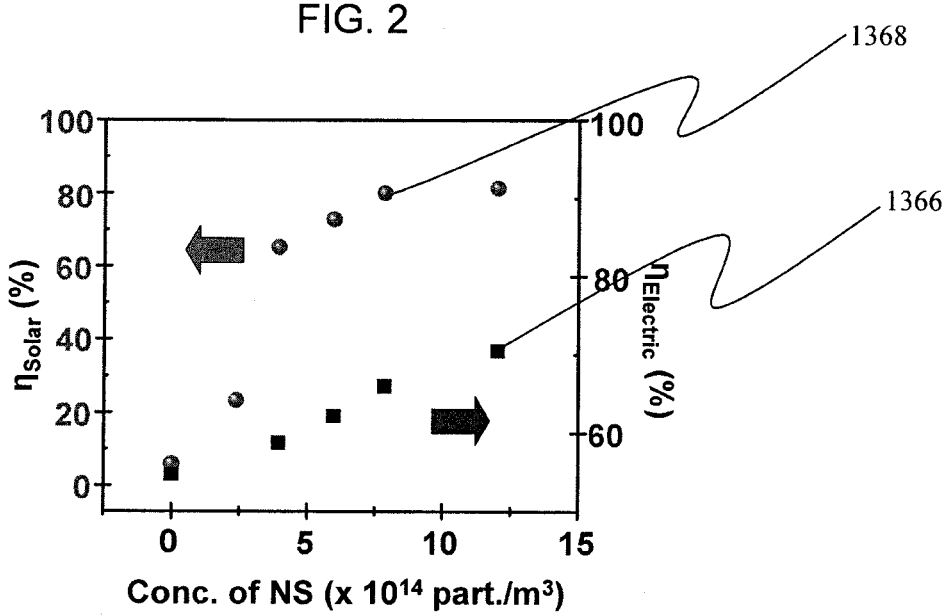
FIG. 13A-13B shows a chart of the energy capture efficiency in accordance with one or more embodiments of the invention.
Figure 13A:
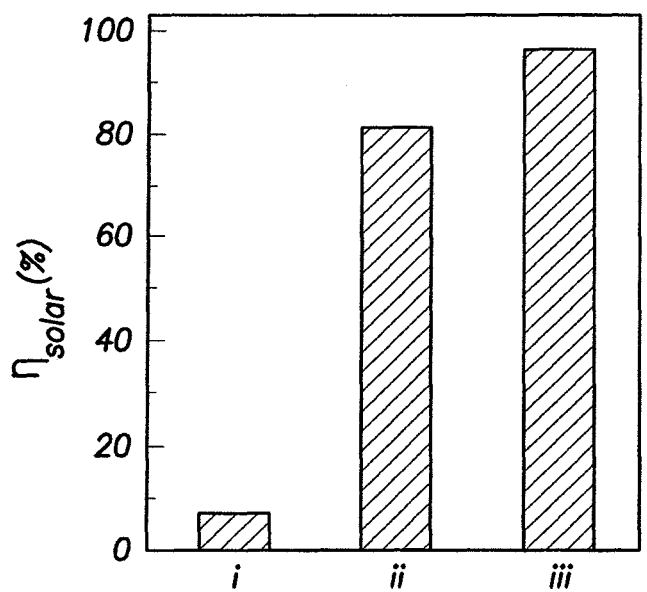

FIG. 13A is a chart of the solar trapping efficiency in accordance with one or more embodiments of the invention. To quantify the energy trapping efficiency of the complex, steam is generated in a flask and throttled through a symmetric convergent-divergent nozzle. The steam is then cooled and collected into an ice bath maintained at 0° C. The nozzle serves to isolate the high pressure in the boiler from the low pressure in the ice bath and may stabilize the steam flow. Accordingly, the steam is allowed to maintain a steady dynamic state for data acquisition purposes. In FIG. 13A, the solar energy capture efficiency (11) of water (i) and Eu2O3-coated nanoshells (ii) and gold branched (ii) nanostructures is shown. The resulting thermal efficiency of steam formation may be estimated at 80% for the coated nanoshell complex and 95% for a gold branched complex. By comparison, water has approximately 10% efficiency under the same conditions.

In one or more embodiments of the invention, the concentration of the complex may be modified to maximize the efficiency of the system. For example, in the case where the complex is in solution, the concentration of the different nanostructures that make up the complex for absorbing EM radiation may be modified to optimize the absorption and, thus, optimize the overall efficiency of the system. In the case where the complex is deposited on a surface, the surface coverage may be modified accordingly.

In FIG. 13B, the steam generation efficiency versus gold nanoshell concentration for solar and electrical heating in accordance with one or more embodiments of the invention is shown. The results show an enhancement in efficiency for both electrical 1366 and solar 1368 heating sources, confirming that the bubble nucleation rate increases with the concentration of complex. At high concentrations, the complex is likely to form small aggregates with small inter-structure gaps. These gaps may create "hot spots", where the intensity of the electric field may be greatly enhanced, causing an increase in temperature of the surrounding water. The absorption enhancement under electrical energy 1366 is not as dramatic as that under solar power 1368 because the solar spectrum includes energetic photons in the NIR, visible and UV that are not present in the electric heater spectrum. At the higher concentrations, the steam generation efficiency begins to stabilize, indicating a saturation behavior. This may result from a shielding effect by the particles at the outermost regions of the flask, which may serve as a virtual blackbody around the particles in the bulk solution.

Figure 14:
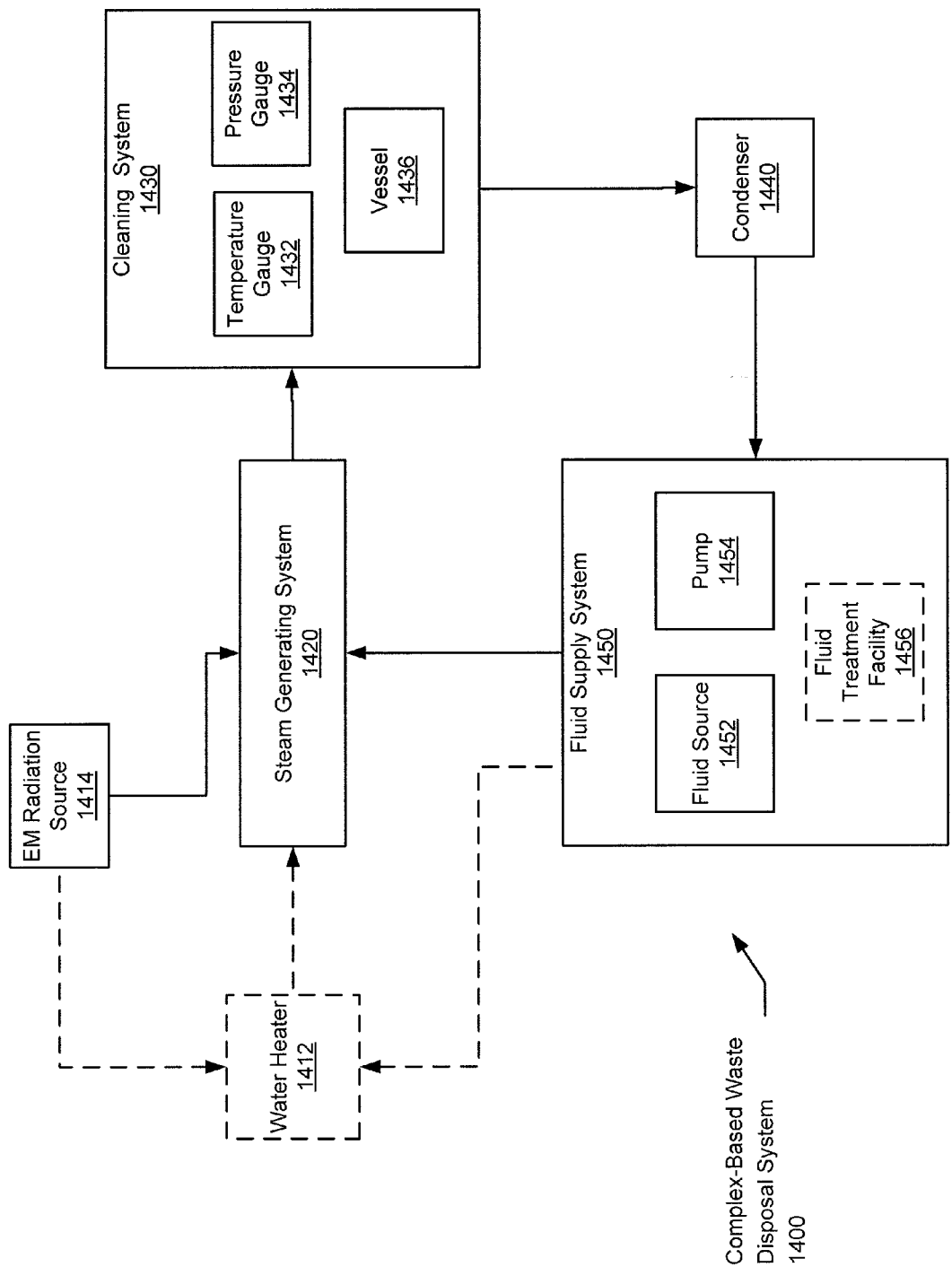
FIG. 14 shows a system in accordance with one or more embodiments of the invention.

FIG. 14 shows a complex based waste disposal system 1400 for creating vapor for waste disposal in accordance with one or more embodiments of the invention. The complex based waste disposal system 1400 includes an EM radiation source 1414, a steam generating system 1420, a cleaning system 1430, a condenser 1440, and a fluid supply system 1450. The complex based waste disposal system may optionally include a water heater 1412. The steam generating system may also include a concentrator as described below to concentrate the EM radiation from the EM radiation source 1414. The steam generating system 1420 uses the EM radiation source 1414 and a complex as described previously to generate temperature and pressure conditions for sanitization and/or sterilization. The cleaning system 1430 includes temperature gauge 1432, pressure gauge 1434, and a vessel 1436.

The temperature gauge 1432 and pressure gauge 1434 may be used to ensure the necessary temperature and pressure is reached inside the vessel. In one or more embodiments of the invention, the steam generating system 1420 of the waste disposal system 1400 is configured to use the vapor for cleaning an object.

In one or more embodiments of the invention, the object to be cleaned and/or disposed of may be placed in the vessel 1436, and vapor at the appropriated temperature and pressure may be used to clean the object. The fluid supply system 1450 includes a fluid source 1452, a pump 1454, and, optionally, a fluid treatment facility 1456. One of ordinary skill in the art will appreciate that embodiments of the invention are not limited to the configuration shown in FIG. 1400. In one embodiment of the invention, the object may be medical waste, fabric, medical equipment, fecal matter, any other object that needs to be cleaned, sanitized, sterilized, disposed of, or any combination thereof.

In one or more embodiments of the invention, the complex based waste disposal system 1400 may include a water heater 1412. The water heater 1412 may be used to preheat the fluid prior to generating steam in the steam generating system 1420.

For each component shown in FIG. 1400, as well as any other component implied and/or described but not shown in FIG. 1400, may be configured to receive material from one component (i.e., an upstream component) of the complex based waste disposal system 1400 and send material (either the same as the material received or material that has been altered in some way (e.g., vapor to fluid)) to another component (i.e., a downstream component) of the waste disposal system 1400. In all cases, the material received from the upstream component may be delivered through a series of pipes, pumps, valves, and/or other devices to control factors associated with the material received such as the flow rate, temperature, and pressure of the material received as it enters the component. Further, the fluid and/or vapor may be delivered to the downstream component using a different series of pipes, pumps, valves, and/or other devices to control factors associated with the material sent such as the flow rate, temperature, and pressure of the material sent as it leaves the component.

In one or more embodiments of the invention, the EM radiation source 1414 is some other natural and/or manmade source, including but not limited to the sun, a light bulb, or any other EM radiation source capable of generating EM radiation. The EM radiation source may be external to the steam generating system 1420. The EM radiation source 1414 may also be a suitable combination of sources of EM radiation, whether emitting energy using the same wavelengths or different wavelengths.

Optionally, in one or more embodiments of the invention, the EM radiation source includes a concentrator used to intensify the energy emitted by the EM radiation source 1414. Examples of an EM radiation concentrator include, but are not limited to, a lens(es), a parabolic trough(s), black paint, or any suitable combination thereof. The EM radiation concentrator may be used to increase the rate at which the EM radiation is absorbed by the complex.

In one or more embodiments of the invention, the steam generating system 1420 of the waste disposal system 1400 is configured to transform (i.e., convert) the fluid into vapor. In one or more embodiments, the steam generating system may be directly connected to, or a part of the vessel 1436. The vessel 1436 of the cleaning system 1430 may include the complex used to heat the fluid. The vessel 1436 may include a liquid solution (or some other material, liquid or otherwise)

that includes the complex, be coated on one or more inside surfaces with a coating of the complex, be coated on one or more outside surfaces with a coating of the complex, be constructed of a material that includes the complex, or any combination thereof. The vessel 1436 may also be adapted to facilitate one or more EM radiation concentrators, as described above. The vessel 1436 may be of any size, shape, color, degree of translucence/transparency, or any other characteristic suitable for the amount and type of vapor required to clean an object. For example, the vessel 1436 may be a large, cylindrical tank holding a quantity of solution that includes the complex and with a number of lenses (acting as EM radiation concentrators) along the lid and upper walls. In such cases, the solution may include the fluid being used to be transformed into vapor. Further, in such cases, the fluid includes properties such that the complex remains in the solution when a filtering system (described below) is used. Alternatively, the steam generating system 1420 may include a translucent pipe with the interior surfaces coated with a substrate of the complex, where the pipe is positioned at the focal point of a parabolic trough (acting as an EM radiation concentrator) made of reflective metal.

In one or more embodiments of the invention, the vessel 1436 includes one or more temperature gauges 1432 to measure a temperature at different points inside the vessel 1436. For example, a temperature gauge 1432 may be placed at the point in the vessel 1436 where the vapor enters or exits the vessel 1436. Such temperature gauge 1432 may be operatively connected to a control system (not shown) used to control the amount and/or quality of vapor produced for generating electric power. In one or more embodiments of the invention, the vessel 1436 may be pressurized where the pressure is read and/or controlled using a pressure gauge 1434. Those skilled in the art will appreciate one or more control systems used to generate steam for waste disposal may involve a number of devices, including but not limited to temperature gauges, pressure gauges, pumps, fans, and valves, controlled (manually and/or automatically) according to a number of protocols and operating procedures.

In one or more embodiments of the invention, the vessel 1436 may also include a filtering system located inside the vessel 1436 to capture impurities in the fluid that are not converted to vapor with the fluid. The filtering system may vary, depending on a number of factors, including but not limited to the configuration of the vessel 1436, the purity requirements of the vapor. The filtering system may be integrated with the control system. For example, the filtering system may operate within a temperature range or pressure range as measured by one or more temperature gauges 1432 and/or pressure gauges 1434.

In one or more embodiments of the invention, the condenser 1440 of the waste disposal system 1400 is configured to condense the vapor used in the cleaning of an object to a fluid. The fluid condensed by the condenser 1440 may be the same as the fluid used in the steam generating system 1420 described above. The condenser 1440 may use air, water, or any other suitable material/medium to cool the vapor. The condenser 1440 may also operate under a particular pressure, such as under a vacuum. Those skilled in the art will appreciate that the condenser 1440 may be any type of condenser, now known or to be discovered, adapted to liquefy a vapor.

In one or more embodiments of the invention, the fluid supply system 1450 is configured to supply fluid to the steam generating system 1420. The fluid source 1452 of the fluid supply system 1450 may be any source of fluid. For example, the fluid source 1452 may include, but is not limited to, the condenser 1440, a pond, a lake, a chemical mixing tank, recycled fluid from a closed-loop system (described below), some other suitable source, or any combination thereof. The flow of fluid to and/or from the fluid source 1452 may be controlled by one or more pumps 1454, which may operate manually or automatically (as with a control system, described above). Each pump 1454 may operate using a variable speed motor or a fixed speed motor.

Optionally, in one or more embodiments of the invention, the fluid treatment facility 1456 is used to treat the fluid received by the fluid supply system 1450 so that the fluid includes characteristics (e.g., pH, mixture of elements and/or compounds, temperature) required by the waste disposal system 1400. The fluid treatment facility 1456 may include any equipment necessary to treat the fluid, including but not limited to a mixing vat, a centrifuge, a chemical separator, and a temperature-controlled holding tank.

Figure 15:
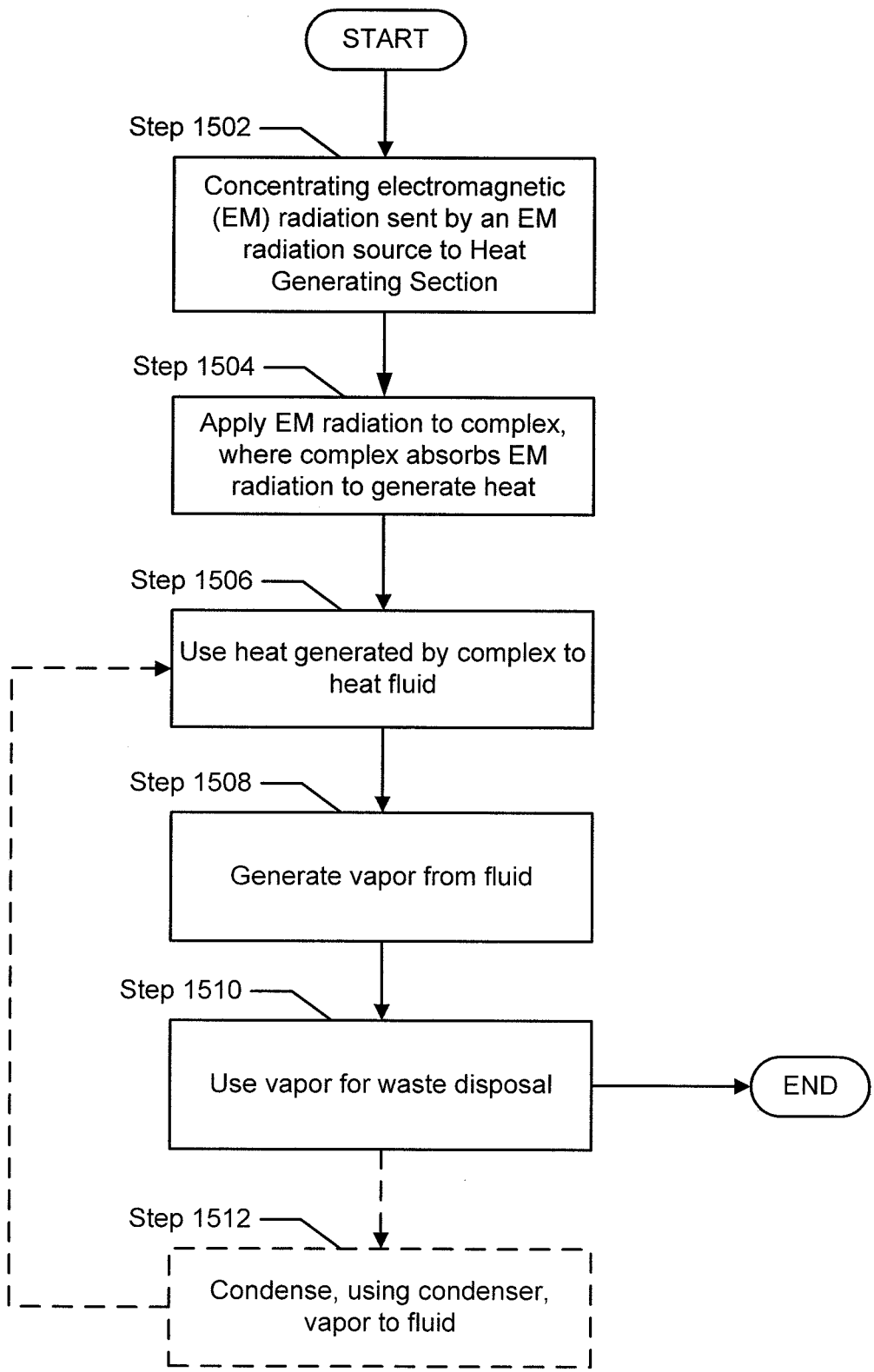
FIG. 15 shows a flowchart for a method of creating vapor for waste disposal in accordance with one or more embodiments of the invention.

FIG. 15 shows a flowchart for a method of creating vapor for waste disposal in accordance with one or more embodiments of the invention. While the various steps in this flowchart are presented and described sequentially, one of ordinary skill will appreciate that some or all of the steps may be executed in different orders, may be combined or omitted, and some or all of the steps may be executed in parallel. Further, in one or more of the embodiments of the invention, one or more of the steps described below may be omitted, repeated, and/or performed in a different order. In addition, a person of ordinary skill in the art will appreciate that additional steps, omitted in FIG. 15, may be included in performing this method. Accordingly, the specific arrangement of steps shown in FIG. 15 should not be construed as limiting the scope of the invention.

Referring to FIG. 15, in Step 1502, EM radiation from an EM radiation source is concentrated and sent to the steam generating system. In Step 1504, the EM radiation irradiates a complex. The complex absorbs the EM radiation and generates heat. The heat is then used to heat a fluid in Step 1506. The fluid may be any liquid, such as water. The fluid may have impurities (e.g., other elements and/or compounds) that are not needed or wanted when the fluid is in vapor form. The vessel containing the fluid may be any container capable of holding a volume of the fluid. For example, the vessel may be a pipe, a chamber, or some other suitable container. In one or more embodiments of the invention, the vessel is adapted to maintain its characteristics (e.g., form, properties) under high temperatures and pressures for extended periods of time. The complex may be part of a solution inside the vessel, a coating on the outside of the vessel, a coating on the inside of the vessel, integrated as part of the material of which the vessel is made, integrated with the vessel in some other way, or any suitable combination thereof. The fluid may be received in the vessel using a pump, a valve, a regulator, some other device to control the flow of the fluid, or any suitable combination thereof.

In one or more embodiments of the invention, the EM radiation is concentrated using an EM radiation concentrator, as described above with respect to FIG. 14. For example, the EM radiation may be concentrated using a lens or a parabolic trough. In one or more embodiments of the invention, the EM radiation is concentrated merely by exposing the vessel to the EM radiation.

In one or more embodiments of the invention, the complex absorbs the EM radiation to generate heat. The EM radiation may be applied to all or a portion of the complex located in the vessel. The EM radiation may also be applied to an intermediary, which in turn applies the EM radiation (either directly or indirectly, as through convection) to the complex. A control system using, for example, one or more temperature gauges, may regulate the amount of EM radiation applied to the complex, thus controlling the amount of heat generated by the complex at a given point in time. Power required for any component in the control system may be supplied by any of a number of external sources (e.g., a battery, a photovoltaic solar array, alternating current power, direct current power).

In Step 1508, the fluid is transformed into a vapor. In one or more embodiments of the invention, the heat generated by the complex is used to heat the fluid to any temperature at or beyond the boiling point of the fluid. In Step 1510, the vapor is applied to an object and, thus, used for the sanitization, sterilization, or destruction (in the case of waste disposal) of an object. After completing Step 1510, the process may end.

Optionally, after completing Step 1510, the process proceeds to Step 1512, where the vapor is condensed to a fluid. In one or more embodiments of the invention, a condenser is used to condense the vapor to a fluid. The fluid may be substantially the same fluid as the fluid described above with regard to Step 1506. After completing Step 1512, the process proceeds to Step 1506. Optional Step 1512 is used as part of a recirculation or closed-loop system.

Figure 16:
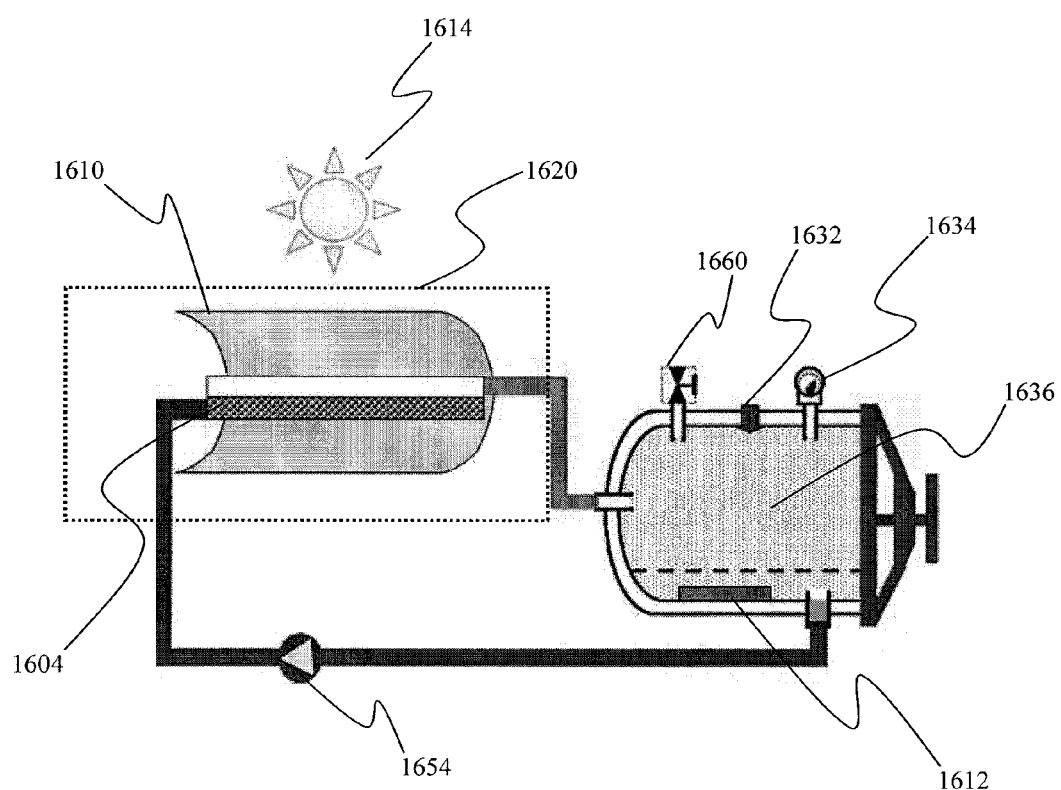
FIG. 16 shows an example system for creating vapor for waste disposal in accordance with one or more embodiments of the invention.

Consider the following example, shown in FIG. 16, which describes a system that produces steam used to clean an object in accordance with one or more embodiments described above. The EM radiation source 1614 irradiates the complex 1604 through the use of the concentrator 1610 as part of the complex based steam generating system 1620. In this specific embodiment, the concentrator 1610 is parabolic mirror concentrating the EM radiation from the EM radiation source 1614 to a vessel containing the complex 1604. The complex based steam generating system 1620 may be used to supply steam to the chamber 1636. The chamber 1636 may include a temperature sensor 1632, a pressure sensor 1634, and a safety valve 1660. The chamber may also optionally include a heater 1612.

In one or more embodiments of the invention, the steam is generated in the complex based steam generating system 1620 and then used to clean an object placed inside the chamber 1636. One of ordinary skill will appreciate that the chamber 1636 may include valves to isolate the chamber 1636 from the rest of the apparatus for the insertion or removal of the object in the chamber 1636. At the conclusion of a cleaning cycle, a pump 1654 may be used to recycle the fluid for the next cleaning cycle. Alternatively, the pump 1654 may be used during the cleaning cycle to maintain the appropriate temperature and pressure necessary for the cleaning of the object.

Figure 17:
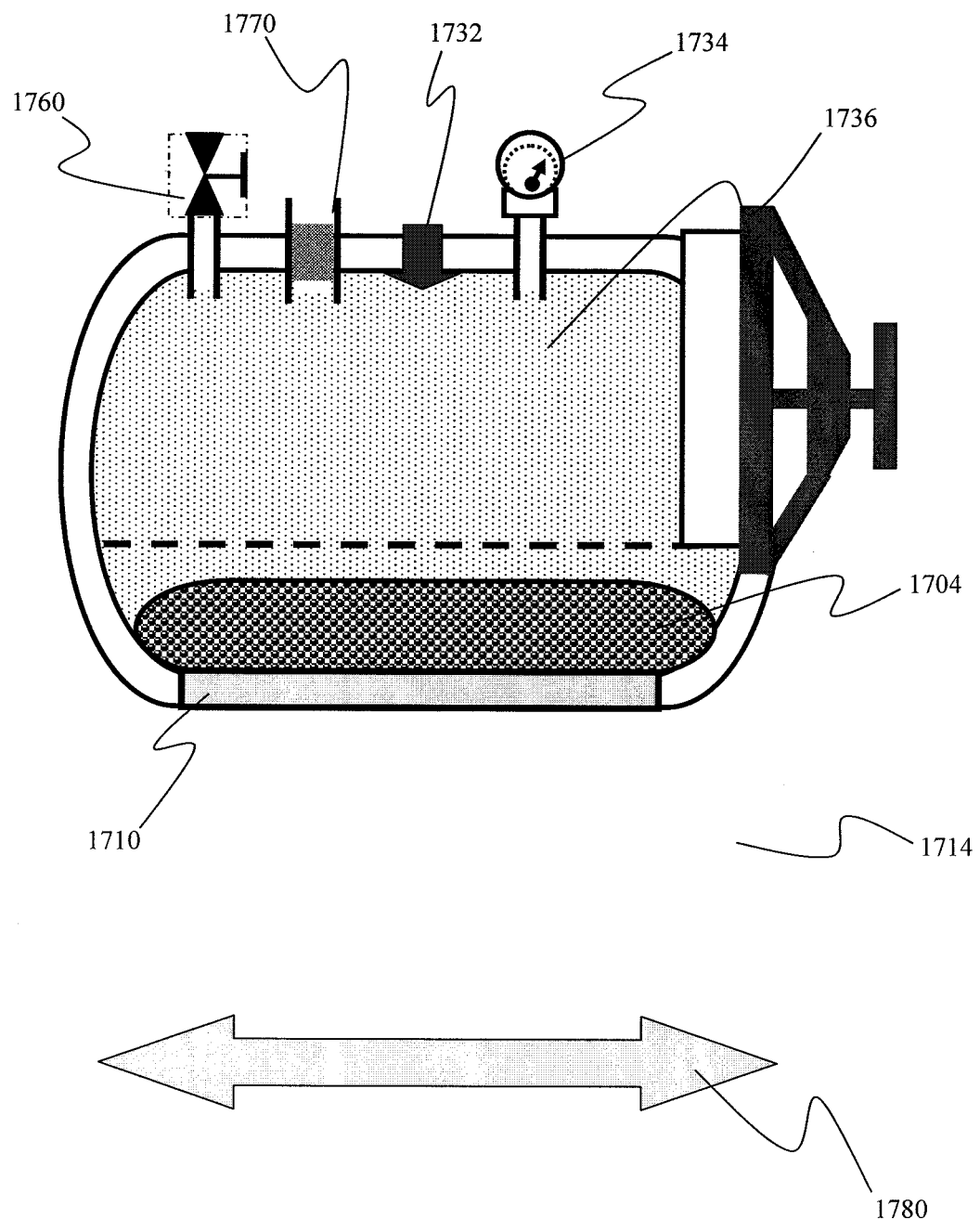
FIG. 17 shows an example of a system in accordance with one or more embodiments of the invention.

FIG. 17 illustrates an alternative configuration of the complex based waste disposal system in accordance with one or more embodiments of the invention. The system shown in FIG. 17 includes a chamber 1736 with a temperature sensor 1732, a pressure sensor 1734, a supply valve 1770, and a safety valve 1760. The supply valve 1770 may be used to supply or maintain the supply of fluid in the chamber 1736. The complex 1704 may be disposed inside the chamber 1736, with the complex being accessible to EM radiation 1714, via the concentrator 1710. In one or more embodiments of the invention, the concentrator may be a lens or transparent material capable of handling the temperatures and pressures necessary to clean or dispose of an object disposed within the chamber 1736. One or more embodiments of the invention may include an optical system 1780 designed to direct the EM radiation 1714 to the complex 1704, depending on the relative position of the EM radiation source. In one or more embodiments of the invention, such as that shown in FIG. 17, the system may be self-contained and portable.

Figure 18:
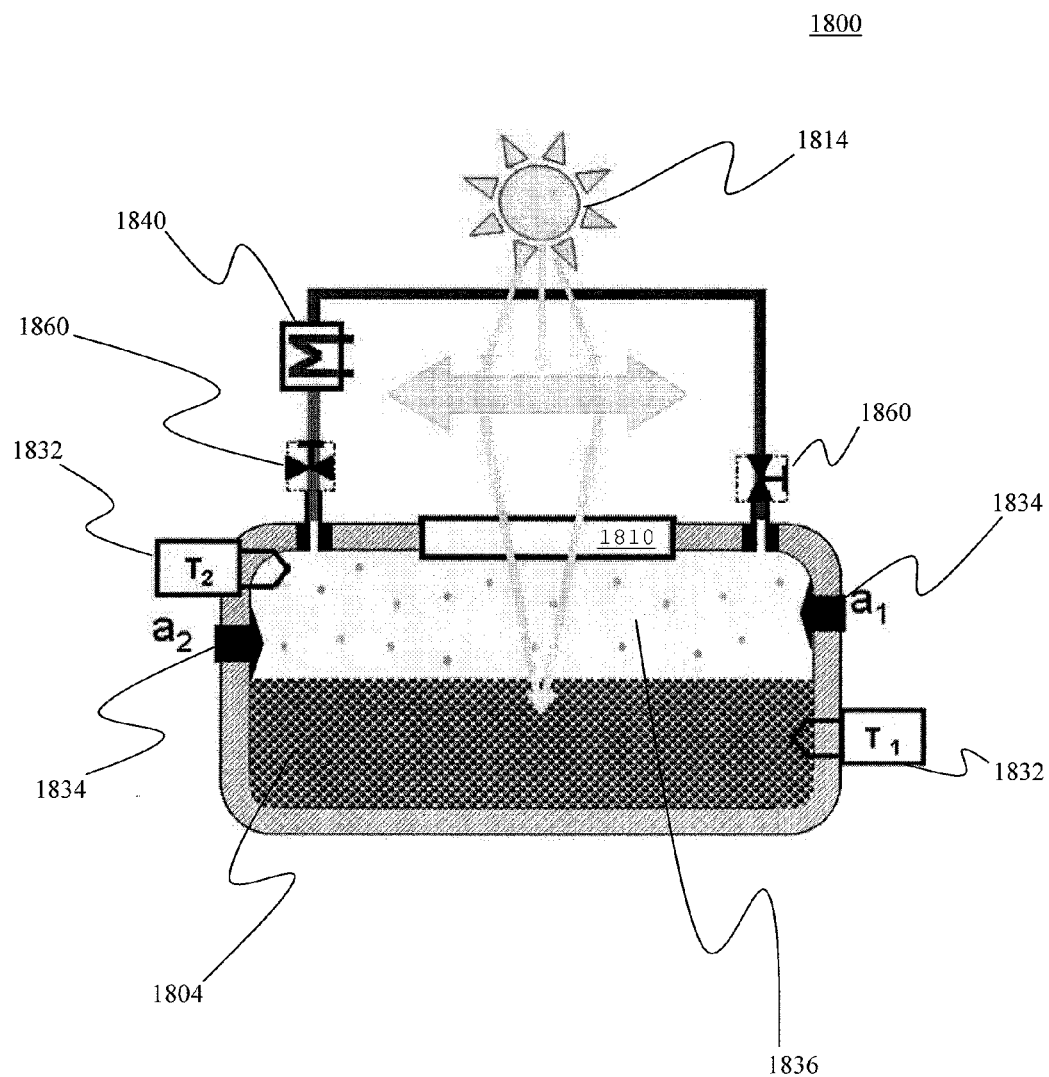
FIG. 18 shows an example of a system in accordance with one or more embodiments of the invention.

FIG. 18 illustrates a system for waste disposal in accordance with one or more embodiments of the invention. The system 1800 includes an EM radiation source 1814 that applies the radiation, via a concentrator 1810, to a complex 1804 located within the chamber 1836. The closed loop system 1800 may include one or more temperature sensors 1832, pressure sensors 1834, and safety valves 1860. The safety valves 1860 may open or close a loop containing a condenser 1840. During operation, an object may be disposed inside the chamber 1836, at a position so as not to impede the EM radiation from the EM radiation source 1814 reaching the complex 1804. The EM radiation from the EM radiation source 1814 is absorbed by complex 1804. As a result of the irradiation, the complex 1804 generates heat in the chamber 1836 and, thus, increases the temperature of the fluid in the chamber 1836 and pressure in the chamber 1836. The fluid is converted to steam and may be applied to the object for sterilization, waste disposal, or sanitation.

FIGS. 19A-19B illustrate the temperature and pressure that may be achieved in one of the embodiments described by FIG. 18. In FIG. 19A, the complex is a gold branched structure as described above in relation to FIGS. 8-11. The EM radiation source is the sun. In FIG. 19A, the safety relief valve begins to vent to the atmosphere when the solution inside the chamber reaches ~170° C. and the pressure reaches ~110 psi. In FIG. 19A, the temperature of the solution 1901 as a function of time indicates that the system may safely reach autoclave conditions. FIG. 19A also includes the temperature as a function of time before 1903 and after 1905 the condenser 1840. FIG. 19B is the pressure 1907 inside the chamber 1836 as a function of time. The irregularity of the pressure and temperature curves shown in FIGS. 19A and 19B are a result of clouds momentarily obstructing the sunlight which reduce the boiling intensity at different moments.

In one or more embodiments of the invention, the complex based steam generation may used to supplement existing waste disposal or cleaning systems. The complex based system may be used to preheat the fluid used for waste disposal in existing systems.

In one or more embodiments of the invention, the complex based waste disposal system may be a solar, portable system designed to be used in remote locations for the disposal of waste, or the cleaning of objects. For example, sanitization of medical instruments or medical equipment when such facilities are unavailable. One or more embodiments of the invention may be used to clean fecal waste material in remote locations.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:
1. A system, comprising:
a steam generation system comprising a complex, wherein the steam generation system is configured to:
receive water;
concentrate electromagnetic (EM) radiation received from an EM radiation source, apply the EM radiation to the complex, wherein the complex absorbs the EM radiation to generate heat, and
transform, using the heat generated by the complex, the water to steam; and a chamber configured to receive the steam and an object, wherein the object is one selected from a group consisting of medical waste, medical equipment, fabric, and fecal matter, wherein the complex comprises at least one selected from a group consisting of copper nanoparticles, copper oxide nanoparticles, nanoshells, nanorods, carbon moieties, encapsulated nanoshells, encapsulated nanoparticles, and branched nanostructures, wherein the complex comprises an encapsulating layer configured to preserve a plasmon resonance of the complex wherein the encapsulating layer comprises silica, titanium dioxide, europium oxide, titanium, europium, erbium, samarium, praseodymium, dysprosium, or a polymer.

2. The system of claim 1, wherein the steam generation system comprises a concentrator, wherein the concentrator is a lens.

3. The system of claim 1, wherein the steam generation system comprises a concentrator, wherein the concentrator is a curved mirror and wherein the vessel is a section of pipe comprising the complex.

4. The system of claim 1, wherein the complex is coated on at least a portion of an interior surface of the steam generation system.

5. The system of claim 1, wherein the system further comprises:
   a control system comprising:
      a pressure sensor configured to measure a pressure inside the chamber; and
      a valve that opens to release the steam from the chamber.

6. The system of claim 5, wherein the pressure inside the chamber is at least 95 psi.

7. The system of claim 5, wherein the control system further comprises:
   a temperature sensor configured to measure a temperature inside the chamber.

8. The system of claim 7, wherein the temperature inside the chamber reaches at least 347 degrees Fahrenheit.

9. The system of claim 1, wherein the EM radiation comprises at least one selected from a group consisting of EM radiation in an ultraviolet region of an electromagnetic spectrum, in a visible region of the electromagnetic spectrum, and in an infrared region of the electromagnetic spectrum.

10. The system of claim 1, wherein the system is portable.

11. A system, comprising:
   a steam generation system comprising a complex, wherein the steam generation system is configured to:
      receive water;
      concentrate electromagnetic (EM) radiation received from an EM radiation source,
      apply the EM radiation to the complex, wherein the complex absorbs the EM radiation to generate heat, and
      transform, using the heat generated by the complex, the water to steam; and
   a chamber configured to receive the steam and an object, wherein the object is one selected from a group consisting of medical waste, medical equipment, fabric, and fecal matter,
   wherein the complex is a carbon moiety, and
   wherein the thermal efficiency of steam formation by the complex is at least 80%, and
   wherein the complex comprises an encapsulating layer configured to preserve a plasmon resonance of the complex wherein the encapsulating layer comprises silica, titanium dioxide, europium oxide, titanium, europium, erbium, samarium, praseodymium, dysprosium, or a polymer.

12. The system of claim 1, wherein a thermal efficiency of steam formation by the complex is at least 80%.

13. The system of claim 1, wherein the complex is at least two selected from a group consisting of copper nanoparticles, copper oxide nanoparticles, nanoshells, nanorods, carbon moieties, encapsulated nanoshells, encapsulated nanoparticles, and branched nano structures.

* * * * *